United States Patent
Kiss

(10) Patent No.: US 12,390,626 B2
(45) Date of Patent: *Aug. 19, 2025

(54) METHOD OF PRODUCING SUBSTANCES WITH SUPERSATURATED GAS, TRANSDERMAL DELIVERY DEVICE THEREOF, AND USES THEREOF

(71) Applicant: Circularity Healthcare, LLC, Pasadena, CA (US)

(72) Inventor: Norbert Kiss, Woodland Hills, CA (US)

(73) Assignee: Circularity Healthcare, LLC, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/412,063

(22) Filed: Aug. 25, 2021

(65) Prior Publication Data

US 2021/0379347 A1 Dec. 9, 2021

Related U.S. Application Data

(63) Continuation of application No. 16/193,832, filed on Nov. 16, 2018, now abandoned, which is a (Continued)

(51) Int. Cl.
*A61M 37/00* (2006.01)
*A61K 33/00* (2006.01)
*A61M 35/00* (2006.01)

(52) U.S. Cl.
CPC ............ *A61M 37/00* (2013.01); *A61K 33/00* (2013.01); *A61M 35/30* (2019.05); *A61M 2037/0007* (2013.01)

(58) Field of Classification Search
CPC ...... A61M 37/00; A61M 11/04; A61M 35/30; A61M 2037/0007; A61M 35/003;
(Continued)

(56) References Cited

U.S. PATENT DOCUMENTS

| 3,561,433 A | 2/1971 | Kovach |
| 4,370,997 A | 2/1983 | Braithwaite et al. |

(Continued)

FOREIGN PATENT DOCUMENTS

| AT | 007346 U1 | 2/2005 |
| EP | 755689 A1 | 1/1997 |

(Continued)

OTHER PUBLICATIONS

Gowri et al., Manufacturing Technology-I. Book, Pearson Education, 464 pages, cited p. 165, (2007).
(Continued)

*Primary Examiner* — Bhisma Mehta
*Assistant Examiner* — Hamza A Darb
(74) *Attorney, Agent, or Firm* — K&L Gates LLP; Louis C. Cullman; Hal Gibson

(57) ABSTRACT

The present specification disclosed a noninvasive transdermal delivery device that relates generally to a handheld mechanical apparatus for noninvasive transdermal administration of gas, small to large water-soluble (hydrophilic) pharmaceutical agents, vitamins, and other therapeutic agents. Components of such delivery devices, methods of producing a substance comprising a supersaturated amount of a dissolved gas, as well as, methods of administering a therapeutic agent using such delivery devices and methods of treating a disease or condition using such delivery devices are also disclosed.

10 Claims, 8 Drawing Sheets

Related U.S. Application Data continuation of application No. 14/112,896, filed as application No. PCT/US2012/034316 on Apr. 19, 2012, now Pat. No. 10,130,800.

(60) Provisional application No. 61/591,443, filed on Jan. 27, 2012.

(58) Field of Classification Search
CPC ...... A61M 2205/8225; A61M 2202/02; A61M 2202/0225; A61M 2202/03; A61M 2202/04; A61M 2205/8218; A61M 2210/04; A61K 33/00

See application file for complete search history.

(56) References Cited

U.S. PATENT DOCUMENTS

| | | | |
|---|---|---|---|
| 4,694,850 | A | 9/1987 | Fumino |
| 5,318,015 | A | 6/1994 | Mansson |
| 5,399,163 | A | 3/1995 | Peterson |
| 5,569,180 | A | 10/1996 | Spears |
| 5,599,302 | A | 2/1997 | Lilley |
| 5,667,769 | A | 9/1997 | Kuckens et al. |
| 5,834,519 | A | 11/1998 | Spears |
| 5,851,544 | A | 12/1998 | Penska et al. |
| 5,899,880 | A | 5/1999 | Bellhouse et al. |
| 6,059,749 | A | 5/2000 | Marx |
| 6,155,258 | A | 12/2000 | Voege |
| 6,241,802 | B1 | 6/2001 | Spears |
| 6,363,964 | B1 | 4/2002 | Carroll |
| 6,743,211 | B1 | 6/2004 | Prausnitz et al. |
| 6,905,111 | B2 | 6/2005 | Nagasaka et al. |
| 6,943,388 | B1 | 9/2005 | Makita et al. |
| 7,113,821 | B1* | 9/2006 | Sun .................. A61B 5/14514 606/29 |
| 7,152,850 | B2 | 12/2006 | Sakakibara et al. |
| 7,334,598 | B1 | 2/2008 | Hollars |
| 7,429,258 | B2 | 9/2008 | Angel et al. |
| 7,857,167 | B1* | 12/2010 | Hollars .................. F17C 7/00 277/910 |
| 10,130,800 | B2* | 11/2018 | Kiss .................. A61K 33/00 |
| 2002/0040205 | A1 | 4/2002 | Rasor et al. |
| 2003/0065294 | A1 | 4/2003 | Pickup et al. |
| 2003/0083610 | A1 | 5/2003 | McGarth |
| 2004/0087916 | A1 | 5/2004 | Pickup et al. |
| 2006/0041248 | A1 | 2/2006 | Patton et al. |
| 2006/0107830 | A1 | 5/2006 | Miller et al. |
| 2007/0043319 | A1 | 2/2007 | Steven et al. |
| 2008/0058709 | A1 | 3/2008 | Da Silva Freitas |
| 2009/0318890 | A1* | 12/2009 | Levy .................. A61B 17/12109 222/145.5 |
| 2010/0028269 | A1 | 2/2010 | Mueller-Walz et al. |
| 2010/0179461 | A1 | 7/2010 | Cunningham et al. |
| 2010/0206390 | A1 | 8/2010 | Hollars |
| 2010/0282691 | A1 | 11/2010 | Fukai |
| 2010/0305505 | A1* | 12/2010 | Ducharme ............ A61M 11/02 604/118 |
| 2011/0034861 | A1 | 2/2011 | Schaefer |
| 2012/0172788 | A1 | 7/2012 | Torok |
| 2012/0271218 | A1 | 10/2012 | Uhland et al. |
| 2013/0079800 | A1* | 3/2013 | Eckert .................. A61K 33/04 606/190 |
| 2013/0245541 | A1* | 9/2013 | Mantell .................. A61M 5/20 604/24 |
| 2014/0163456 | A1 | 6/2014 | Kiss |
| 2014/0228740 | A1 | 8/2014 | Kiss |

FOREIGN PATENT DOCUMENTS

| | | |
|---|---|---|
| EP | 2246028 A1 | 11/2010 |
| EP | 2455052 A1 | 5/2012 |
| GB | 1297794 A | 11/1972 |
| JP | 11-218297 A | 8/1999 |
| JP | 2005058745 A | 3/2005 |
| JP | 2009254727 A | 11/2009 |
| WO | 2000/001341 A1 | 1/2000 |
| WO | 2001/005445 A2 | 1/2001 |
| WO | 2001/064280 A1 | 9/2001 |
| WO | 2004/043533 A2 | 5/2004 |
| WO | 2006/120461 A1 | 11/2006 |
| WO | 2008/004543 A1 | 1/2008 |
| WO | 2009/126121 A1 | 10/2009 |
| WO | 2010/095067 A1 | 8/2010 |
| WO | 2010/138703 A1 | 12/2010 |
| WO | 2011/007425 A1 | 1/2011 |
| WO | 2012/144990 A1 | 10/2012 |
| WO | 2012/145554 A2 | 10/2012 |
| WO | 2012/145555 A2 | 10/2012 |

OTHER PUBLICATIONS

Singaporean Written Opinion dated Jul. 24, 2015 for Singaporean Patent Application No. 2013077623 filed on Apr. 19, 2011.
Pressure regulator, 2010, cited in Singaporean Written Opinion and retrieved from http://web.archive.org/web/20100402070015/http://en.wikipedia.org/wiki/Pressure_regulator.
Singaporean Written Opinion dated Jul. 24, 2015 for Singaporean Patent Application No. 2013077698 filed on Apr. 19, 2012.
International Search Report and Written Opinion mailed on Mar. 21, 2012 for International Application No. PCT/US2011/033060 filed on Apr. 19, 2011.
Singaporean Written Opinion mailed on Jan. 21, 2015 for Singaporean Patent Application No. 2013077623 filed on Apr. 19, 2011.
Singaporean Written Opinion mailed on Dec. 15, 2014 for Singaporean Patent Application No. 2013077706 filed on Apr. 19, 2012.
Extended European Search Report mailed on Sep. 11, 2014 for European Patent Application 1186376.4 filed on Apr. 19, 2011.
International Search Report and Written Opinion for International Application No. PCT/US2012/034316 filed on Apr. 19, 2012.
International Search Report and Written Opinion for International Application No. PCT/US2012/034314 filed on Apr. 19, 2012.
Singaporean Written Opinion mailed on Jan. 21, 2015 for Singaporean Patent Application No. 2013077698 filed on Apr. 19, 2012.

\* cited by examiner

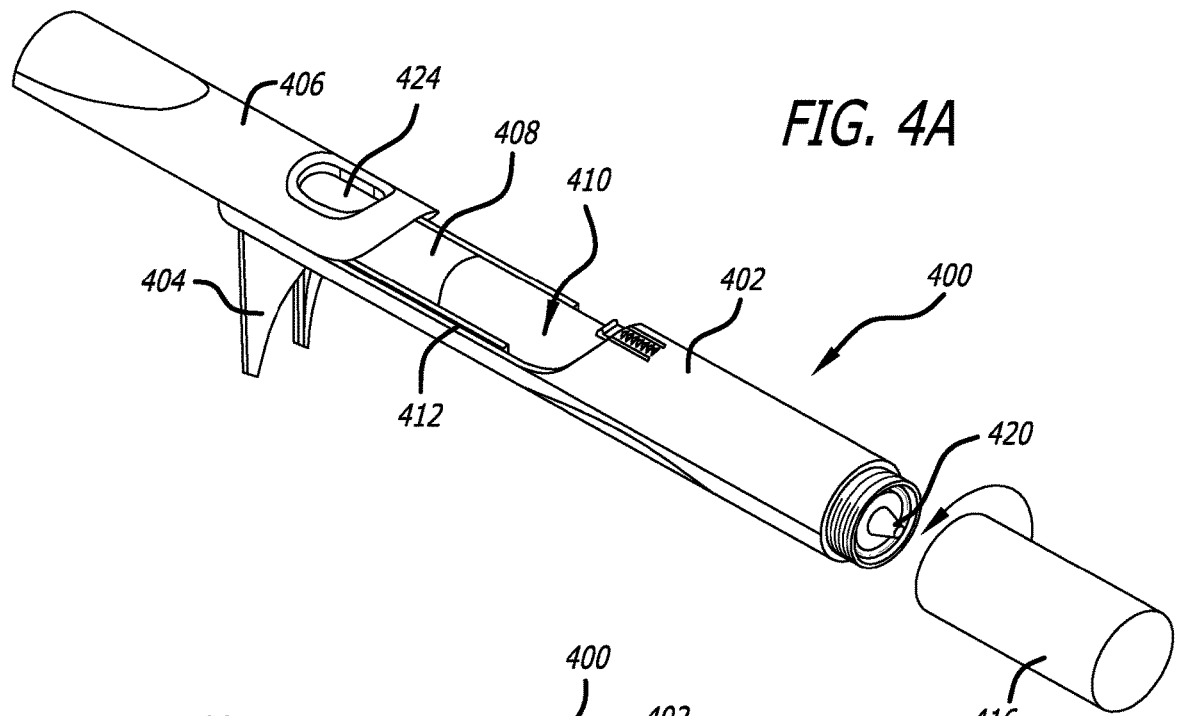
FIG. 4A
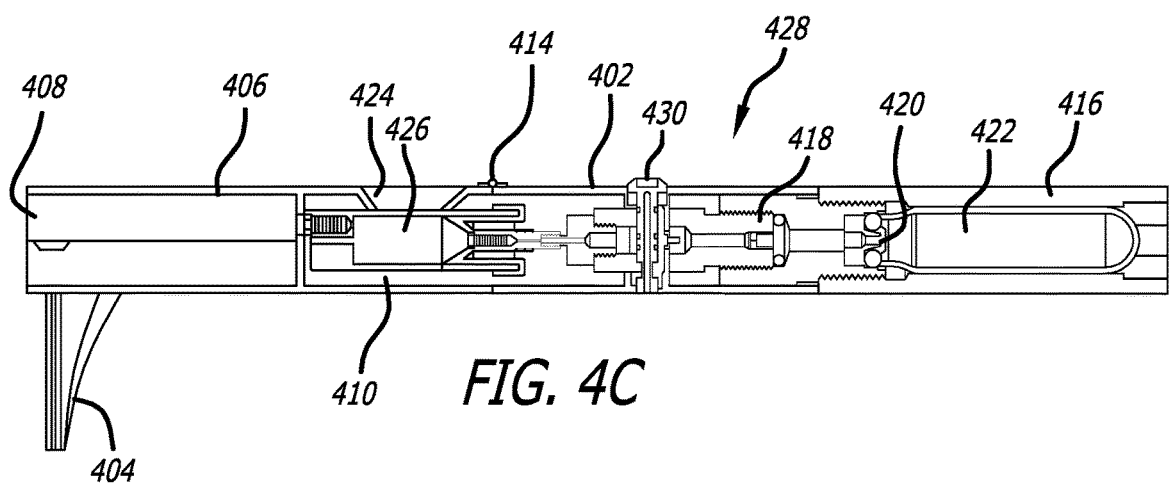
FIG. 4B
FIG. 4C

METHOD OF PRODUCING SUBSTANCES WITH SUPERSATURATED GAS, TRANSDERMAL DELIVERY DEVICE THEREOF, AND USES THEREOF

The present application is a continuation of U.S. Pat. No. 16/193,832, filed Nov. 16, 2018, which is a continuation of U.S. Pat. No. 14/112,896, filed Oct. 18, 2013, now U.S. Pat. No. 10,130,800B2, issued Nov. 20, 2018, which is a national phase of PCT/US2012/034316 filed Apr. 19, 2012, and claims the benefit of PCT/US2011/033060 filed on Apr. 19, 2011, and U.S. Provisional Application Ser. No. 61/591,443 filed Jan. 27, 2012, the entire disclosures of each of which are incorporated by reference herein.

INTRODUCTION

Delivery of an agent through the skin to achieve a therapeutic effect is commonly known as transdermal drug delivery. Transdermal drug delivery systems are dosage forms that facilitate transport of a therapeutic agent to viable epidermal and or dermal tissues of the skin for local therapeutic effect as well as systemically via blood circulation. Transdermal delivery of a therapeutic agent provides several advantages over injectable and oral routes. For example, transdermal delivery of a therapeutic agent increases bioavailability of the agent by avoiding gastrointestinal absorption and hepatic first pass metabolism, enhances therapeutic efficiency of the agent by providing controlled, constant administration of the agent, maintains a steady plasma level of the agent by providing continuous administration of the agent, reduces pharmacological dosing due better absorption of the agent, and provides better overall treatment value through greater administration flexibility and increase patient compliance. Disadvantages of transdermal delivery include, e.g., difficulty in administering therapeutic agents with a molecular weight greater than 500 Daltons or use of therapeutic agents with a very low or high partition coefficient.

A transdermal drug delivery system may be of an active or a passive design. Common dosage forms of a passive transdermal drug delivery system include, e.g., ointments, creams, gels, and transdermal patches. Passive systems require careful selection of a base and addition of penetration enhancers and are applied the skin surface to deliver a specific dose of agent into the blood stream. Because of the impervious nature of the skin, passive transdermal drug delivery systems have typically been used with lipophilic therapeutic agents.

An active transdermal drug delivery system uses mechanical energy to increase therapeutic agent transport across the skin by either altering the skin barrier (primarily the stratum corneum) or increasing the agent's energy. Such active systems include, e.g., microneedles and microdermabrasion which puncture or otherwise physically disrupt the stratum corneum, photochemical waves which use chemicals to alter the stratum corneum, iontophoresis which uses low voltage electrical current to drive charged agents through the skin, electroporation and reverse electrporation which use short high voltage electrical pulses to create transient aqueous pores in the skin, sonophoresis which uses low frequency ultrasonic energy to disrupt the stratum corneum, thermal ablation which uses heat to make the skin more permeable and to increase the agent's energy, and magnetophoresis which uses magnetic energy to increase drug flux across the skin.

There are two important layers in skin: the dermis and the epidermis. The outermost layer, the epidermis, is approximately 100 to 150 micrometers thick, has no blood flow and includes a layer within it known as the stratum corneum. This layer is important to transdermal delivery as its composition provides for water retention and foreign substance defense. Beneath the epidermis, the dermis contains a system of capillaries that transport blood throughout the body. If the drug is able to penetrate the stratum corneum, it can enter the blood stream. Although sweat ducts and hair follicles are also paths of entry into the blood system, these avenues have been considered rather insignificant. See, e.g., Aulton, Pharmaceutics: The Science of Dosage Form Design (2d edition, Churchill Livingston, Harcourt publishers, 2002).

The transdermal route has become one of the most successful and innovative focus's for research in drug delivery. Over 35 therapeutic agents have now been approved for sale in the U.S., and approximately 16 active ingredients have been approved for use globally. However, there is still a need for better ways to deliver a therapeutic agent by the transdermal route. For example, transdermal delivery systems on the market today are limited to small molecular weight drugs with very small daily dosages often companied by various patient discomforts. The present specification discloses a transdermal delivery system that uses a device to administer a vapor comprising liquid particles including a supersaturated amount of a dissolved therapeutic agent that enters the circulatory system via the sweat gland pore and duct system.

SUMMARY

Thus, aspects of the present specification disclose a transdermal device. A transdermal delivery device disclosed herein can comprise a pressure cylinder, a permeation valve, an exchange chamber and a treatment chamber. The above components can be fitted within a housing.

Other aspects of the present specification disclose a vapor producing assembly within the exchange chamber. A vapor producing assembly disclosed herein can comprise a permeation valve and a fluid chamber assembly. A vapor producing assembly disclosed herein may optionally comprise a control switch assembly.

Yet other aspects of the present specification disclose a method of producing a substance comprising a supersaturated amount of dissolved gas. A method of producing a substance disclosed herein comprises the steps of placing a substance as disclosed herein into an air-tight container; and exposing the substance to gas, wherein upon exposure, the gas dissolves into the substance in an amount greater than the substance could dissolve at 25° C. and 1 atm. The gas may be carbon dioxide. The resulting substance supersaturated with the dissolved gas can then be administered to an individual to treat a condition as disclosed herein. In another aspect, the present specification discloses a use of a substance comprising a supersaturated amount of dissolved gas to manufacture a medicament. Such a medicament can then be administered to an individual to treat a condition as disclosed herein.

Still other aspects of the present specification disclose a method of transdermally administering a therapeutically effective amount of therapeutic agent to an individual. A method of transdermal administration disclosed herein comprises the step of administering a substance comprising a supersaturated amount of dissolved gas to an individual using a transdermal delivery device disclosed herein. In another aspect, a method of transdermal administration disclosed herein comprises the step of administering a substance comprising a supersaturated amount of dissolved gas at a rate set by a permeation valve and a therapeutic agent to an individual using a transdermal delivery device disclosed herein. Administration of the gas and/or the therapeutic agent typically treats a symptom associate with a condition. In an aspect, the present specification discloses a use of a substance including a supersaturated amount of dissolved gas to treat a condition using a transdermal device disclosed herein. Aspects also include use of a transdermal delivery device disclosed herein to transdermally administer a therapeutically effective amount of therapeutic agent to an individual.

Further aspects of the present specification disclose a method of treating a condition using a transdermal device disclosed herein. A method of treating a condition disclosed herein comprises the step of administering a composition comprising a substance including a supersaturated amount of dissolved gas using a transdermal delivery device as disclosed herein to a body part of the individual suffering from a condition, wherein the administration of the composition reduces a symptom associated with condition. A method of treating a condition disclosed herein also comprises the step of administering a composition comprising a substance including a supersaturated amount of dissolved gas and a therapeutic agent using a transdermal delivery device as disclosed herein to a body part of the individual suffering from a condition, wherein the administration of the composition reduces a symptom associated with condition. A substance may be a liquid aerosol, foam, emulsion, gel, sol, or other substance that can become supersaturated with an amount of dissolved gas. A condition includes, without limitation, an ischemia, a hypertension, a cardiovascular disorder, treating a diabetic disorder, a wound, a chronic inflammation, an arthritis, a migraine, a cellulite disorder, a pale skin disorder, and a cosmesis disorder. In an aspect, the present specification discloses a use of a substance including a supersaturated amount of dissolved gas to treat a condition. A transdermal device disclosed herein may be used to administer the substance over a set period of time at a set rate based on gas cylinder pressure and permeation valve rate. Aspects also include use of a transdermal delivery device disclosed herein to transdermally administer a therapeutically effective amount of therapeutic agent to treat a condition in an individual to an individual.

BRIEF DESCRIPTION OF THE DRAWINGS

The figures are exemplary of different embodiments of the subject matter disclosed herein. Each illustrated embodiment is not intended to limit the scope of the subject matter disclosed herein, but rather, be exemplary to the scope and spirit of it. Like components in the figures share identical numbering.

FIG. 4A illustrates a perspective view of an exemplary transdermal delivery device.

FIG. 4B illustrates a cross-section of an exemplary transdermal delivery device.

FIG. 4C illustrates a cross-section of another exemplary transdermal delivery device including an actuator.

DETAILED DESCRIPTION

The average diameter of most human sweat glands offers adequate space for most drug molecules to pass through. According to various studies, the average density of sweat pores varies greatly with the individual and body site. The palmer surfaces, palms and finger, and the plantar surfaces, soles of the feet and the toes have an average of 2,700 pores per square inch of ridge friction skin surface. This compares to approximately 400 pores per square inch of the balance of the body's skin surface. The total number of sweat pores distributed over the entire body has been estimated at from 1.6 to four million. The size of the sweat gland has been found to vary as much as fivefold between individuals but on average the pore size in the human skin is 50 microns. The dimension of the coil leading down from the opening in the epidermis is about two to five mm long and about 60 to 80 microns in diameter, with the duct having a slightly smaller diameter.

The present specification discloses lightweight, hand-held mechanical devices designed to transdermally administer therapeutic agents to an individual. The devices can produce a vapor comprising a supersaturated amount of a dissolved gas that is non-invasively delivery through the skin via the pore and duct systems contained within the skin, such as, e.g., the sweat gland pore and duct system. In general operation, a removable cartridge containing a compressed gas, such as, e.g., carbon dioxide is attached to a port of a permeation valve. The permeation valve can reduce the pressure and hence the speed of the gas to a predetermined rate without mechanical adjustment. This regulation of the gas pressure can also reduce the temperature of the gas.

In the case where the gas is a therapeutic agent, this low pressure, ambient temperature gas can then be passed to a fluid chamber assembly containing a liquid, such as, e.g., water, a physiologically buffered solution, or other suitable liquid, where it is dissolved into the liquid producing a liquid supersaturated with the gas. This therapeutic gas is then administered to an individual by vaporizing the supersaturated liquid and applying the vapor to a skin surface where the liquid particles including a supersaturated amount of dissolved therapeutic agent enters into the body via skin pores. In the case where the therapeutic agent is not the gas, this low pressure, ambient temperature gas can be passed to a fluid chamber assembly containing a liquid and the therapeutic agent where the gas is dissolved into the liquid producing a therapeutic liquid including a supersaturated amount of dissolved gas. This therapeutic agent can then be transdermally administered to an individual as a vapor.

Figure 1:
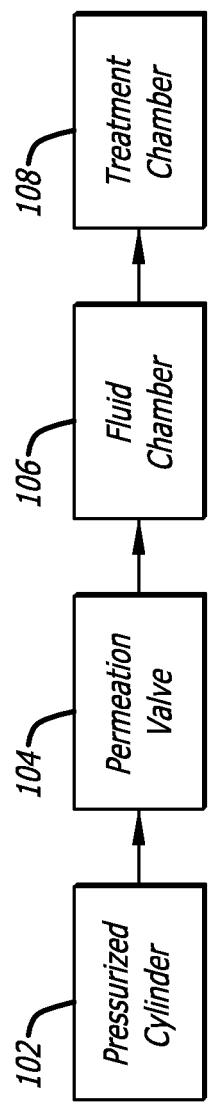
FIG. 1 illustrates a block flow chart of components of an example delivery device described herein.

Aspects of the present specification disclose, in part, a transdermal delivery device. A flow chart of such a device is illustrated in FIG. 1. Such a device can include at least one pressurized cylinder 102, at least one permeation valve 104, fluid chamber 106 and treatment chamber 108. Each of these components can be directly connected or can include additional components in between. For example, a button actuating a valve can be located between permeation valve 104 and fluid chamber 106. Other addition valves or ports can also be included.

A transdermal delivery device disclosed herein can comprise a housing (see, e.g., housing 200 of FIG. 2) and a vapor producing assembly, wherein the housing encloses the vapor producing assembly. Such a device can be designed to be a lightweight, hand-held portable device that provides a practical and comfortable feel for the user during operation of the device. The overall shape of the transdermal delivery device disclosed herein is generally cylindrical in shape, although other geometries can be used. In one embodiment, a transdermal delivery device disclosed herein has a length of less than about 20 inches long, less than about 18 inches long, less than about 16 inches long, less than about 14 inches long, less than about 12 inches long, less than about 10 inches long, or less than about 8 inches long and a width of less than 2 inches, less than 1.5 inches, less than 1 inches, or less than 0.5 inches. In an aspect of this embodiment, a transdermal delivery device disclosed herein can be less than about 12 inches in length and about 1 inch in width.

Figure 2:
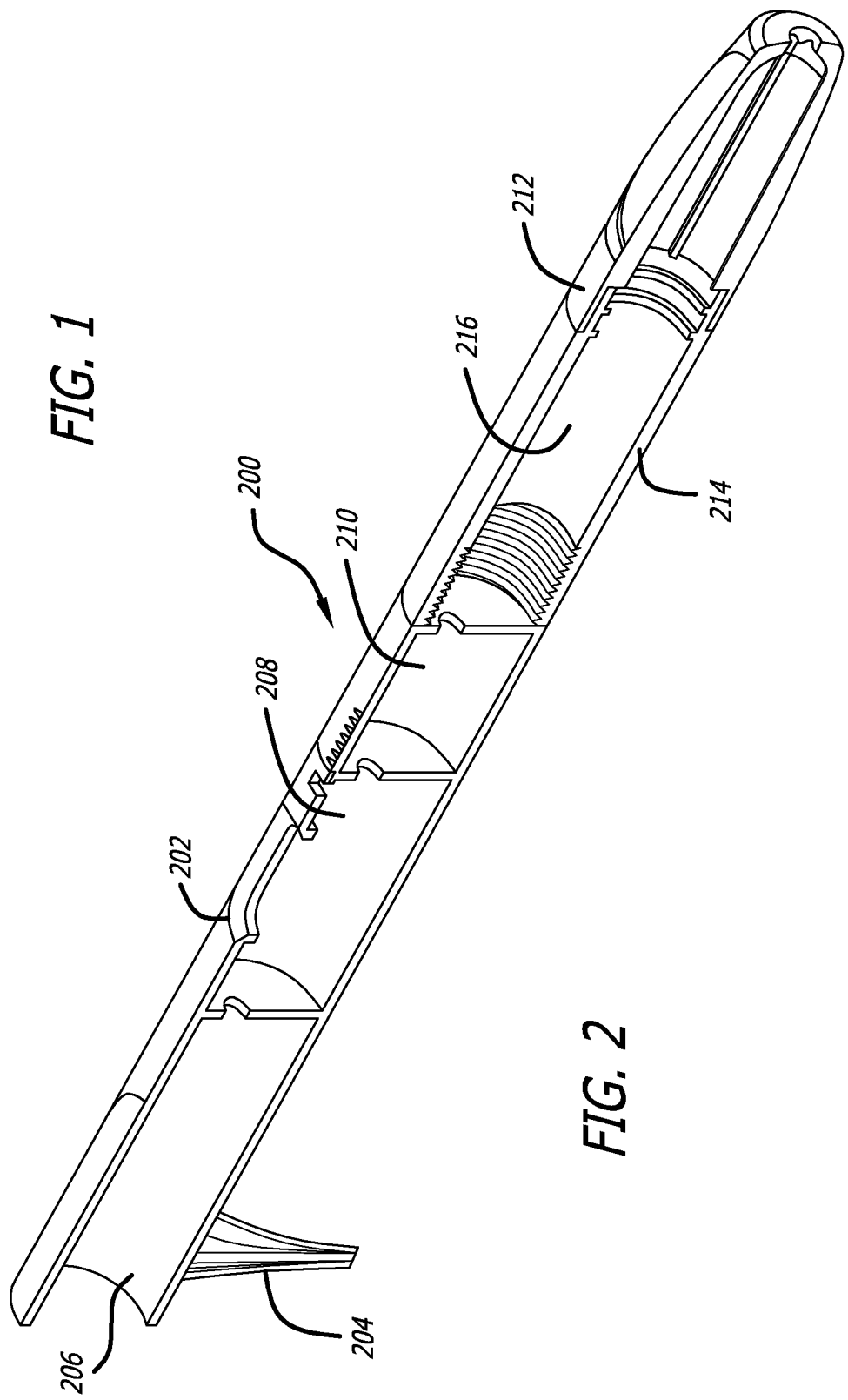
FIG. 2 illustrates a cross-section view of an exemplary housing.

A housing disclosed herein comprises an external body shell (see, e.g., external body shell 202 of FIG. 2), one or more internal compartments and a cartridge retaining container detachably engaged to the external body shell (see, e.g., cartridge retaining container 212 of FIG. 2). An external shell disclosed herein can be made of any durable material that provides for durability, safety, and portability, including a metal or metal alloy, a high-strength plastic, or a composite material. The shape of the external shell is designed to contain a vapor producing assembly disclosed herein and provide a practical and comfortable feel when held in the hand of the user and during operation of the device.

A housing disclosed herein may optionally comprise a fluid chamber assembly access covering detachably engaged with the external body shell. A fluid chamber assembly access covering disclosed herein is designed to provide access to a fluid chamber assembly disclosed herein. A fluid chamber assembly access covering disclosed herein is designed to be detached from the external body shell of the transdermal delivery device. Such detachment allows a user to, e.g., remove a fluid chamber assembly, or component thereof, as well as reattach a fluid chamber assembly, or component thereof. In one embodiment, a fluid chamber assembly access covering disclosed herein is designed to be completely removed from the housing of the transdermal delivery device in order to allow access as disclosed herein. In another embodiment, a fluid chamber assembly access covering disclosed herein is designed to achieve access to the fluid chamber assembly as disclosed herein, but still remain attached to the external body shell of the housing. As a non-limiting example, a fluid chamber assembly access covering may include a threaded portion that can be screwed onto or off of a threaded portion of the external body shell. In such an arrangement, the access covering can be completely removed from the housing. As another non-limiting example, a fluid chamber assembly access covering includes a track and grove arrangement with the external body shell allowing the access covering to slide back and forth from an open to close position. Such an arrangement can be designed to allow complete removal of the access covering or include a stop that prevents complete removal, but provides access as disclosed herein. As yet another non-limiting example, a fluid chamber assembly access covering can include a hinge assembly with the external body shell that allows the access covering to be swung open or closed. In such an arrangement, the access covering typically remained attached to the housing. Other arrangements to allow assess as disclosed herein are known in the art.

The one or more internal compartments disclosed herein are designed to correctly hold a vapor producing assembly, or components thereof, in a manner that ensures proper operation of the transdermal delivery device. An internal compartment can include, without limitation, an open-ended delivery outlet (see, e.g., open-ended delivery outlet 206 of FIG. 2) and a vapor producing assembly compartment (see, e.g., vapor producing assembly compartment 208 of FIG. 2). Such compartments may include internal struts that enhance structural integrity of the device and/or footings that ensure proper placement and function of the vapor producing assembly disclosed herein, or component part thereof.

A cartridge retaining container disclosed herein can comprise an external covering shell (see, e.g., external covering shell 214 of FIG. 2) and an internal cartridge compartment (see, e.g., internal cartridge compartment 216 of FIG. 2). A cartridge retaining container disclosed herein is designed to correctly position, mount, and secure a compressed gas cartridge to a lance housing of a permeation valve during operation of the transdermal delivery device.

A cartridge retaining container disclosed herein can detachably engage the external body shell of the housing. In other embodiments, a cartridge can be built into a device and can provide a single use after which time the device can be discarded. A cartridge retaining container disclosed herein can be designed to be completely removed from the housing of the transdermal delivery device in order to achieve an unengaged position as disclosed herein. In another embodiment, a cartridge retaining container disclosed herein is designed to achieve an unengaged position as disclosed herein, but still remain attached to the housing. As a non-limiting example, a cartridge retaining container may include a threaded portion that can be screwed onto or off of a threaded portion of the external body shell. In such an arrangement, the cartridge retaining container can be completely removed from the housing where a compressed gas cartridge is inserted into an internal cartridge compartment. The cartridge retaining container is then screwed back onto the housing in a manner that allows properly insertion of the cartridge into the device. As another non-limiting example, a cartridge retaining container including a hinge assembly with the external body shell that allows the cartridge retaining container to positioned in a manner that allows a compressed gas cartridge to be properly inserted into the device. In such an arrangement, the cartridge retaining container typically remained attached to the housing. Other arrangements to allow proper cartridge insertion and cartridge retaining container attachment as disclosed herein are known in the art.

A cartridge retaining container disclosed herein can be detachably engaged with the external body shell of the transdermal delivery device. This is achieved in that a cartridge retaining container disclosed herein can be in one of two operational positions. In an unengaged position (or detached or opened position), a cartridge retaining container disclosed herein allows a compressed gas cartridge to be placed in the internal cartridge compartment of the cartridge retaining container, reveals a lance housing present on a permeation valve disclosed herein for a compressed gas cartridge, and/or both. In an engaged position (or attached or closed position), a cartridge retaining container disclosed herein is designed to position, mount, and secure a compressed gas cartridge to a lance housing of a permeation valve in a manner that releases the compressed gas from the cartridge and channels the released gas into the permeation valve where the gas permeates through the valve at a predetermined rate.

A housing disclosed herein may optionally comprise a leg stand or other protrusion attached to the external body shell (see, e.g., leg stand 204 of FIG. 2). A leg stand disclosed herein can typically be located near the end where the open-ended delivery outlet is located. A leg stand disclosed herein can be designed to angle a fluid container assemble to provide a tilt of no greater than 30° relative to a horizontal position of a transdermal delivery device in order to facilitate mixing of the gas and liquid. The leg stand can also be retractable into the external body shell for ease of storage.

Thus, in one embodiment, a housing as disclosed herein can comprise an external body shell, an open-ended delivery outlet including a treatment chamber, a vapor producing assembly compartment including a fluid exchanger, a permeation valve and a cartridge retaining container detachably engaged with the external body shell, wherein the vapor producing assembly compartment intervenes between the open-ended delivery outlet and the cartridge retaining container. The open-ended delivery outlet is designed to receive a body part of an individual such as a finger, toe, or paw. Alternatively, the open-ended delivery outlet may simply be place on top, or in the vicinity of, a skin surface. The vapor producing assembly compartment itself can be subdivided into different compartments designed to contain component parts of the vapor producing assembly disclosed herein.

In another embodiment, a housing disclosed herein comprises an external body shell, an open-ended delivery outlet, a vapor producing assembly compartment comprising a fluid chamber assembly compartment and a permeation valve, and a cartridge retaining container detachably engaged with the external body shell, wherein the linear arrangement of the interior compartments is the open-ended delivery outlet next to the fluid chamber assembly compartment which is next to the permeation valve.

An exemplary device is illustrated in FIG. 2, housing 200 comprises external body shell 202, leg stand 204, open-ended delivery outlet 206, vapor producing assembly compartment 208, permeation valve compartment 210 and cartridge retaining container 212 detachably engaged with external body shell 202, and comprises an external covering shell 214, an internal cartridge compartment 216.

The transdermal device may optionally comprise a compressed gas cartridge which can be housed within cartridge retaining container 212. A compressed gas cartridge disclosed herein is typically of a size sufficient to contain enough gas under pressure to produce a volume of liquid supersaturated with dissolved gas sufficient to produce a vapor that provides a therapeutic effect. The therapeutic effect in some cases can be achieved with one dose of supersaturated gas. The compressed gas cartridge disclosed herein can contain a gas having a pressure exceeding 40 psi (about 275 kPa) at 21.1° C., or regardless of the pressure at 21.1° C., having a pressure exceeding 104 psi (about 717 kPa) at 54.4° C., or any liquid having an absolute vapor pressure exceeding 40 psi (about 275 kPa) at 37.8° C. For example, a compressed gas cartridge containing 16 g, 8 g, or 1.3 g of a food or medical grade gas under a pressure of about 400 kPa (about 58 psi) at 21.1° C., about 600 kPa (about 87 psi) at 21.1° C., about 800 kPa (about 116 psi) at 21.1° C., or about 1000 kPa (about 145 psi) at 21.1° C. In one embodiment, a compressed gas cartridge containing 16 g of food or medical grade carbon dioxide under about 800 kPa of pressure at 21.1° C. The compressed gas cartridge may be of a disposable design. Such a disposable compressed gas cartridge typically includes a permeation seal that can be pierced to release the gas. For example, as disclosed herein, a lance from a permeation valve pierces the permeation seal of a compressed gas cartridge, thereby allowing release of compressed gas from the cartridge into an though the permeation valve in a manner that ensures constant gas flow from the transdermal delivery device.

Non-limiting examples of a gas useful to operate the transdermal delivery device disclosed herein include a food or medical grade gas including a food or medical grade carbon dioxide, a food or medical grade oxygen, a food or medical grade helium, and a food or medical grade argon. A compressed gas cartridge disclosed herein can be threaded or non-threaded. A threaded compressed gas cartridge can be secured to a pressure-temperature regulator assembly without the aid of a cartridge retaining container as disclosed herein. A non-threaded compressed gas cartridge can be secured to a permeation valve using a cartridge retaining container as disclosed herein. A compressed gas cartridge disclosed herein may be of a standard industry design, or may be of a custom design useful solely for the transdermal delivery device disclosed herein. In one embodiment, a threaded or non-treaded compressed gas cartridge comprises a body, an internal gas compartment, and a puncturable seal. In another embodiment, a threaded or non-treaded compressed gas cartridge comprises a body, a neck, an internal gas compartment, and a puncturable seal.

Aspects of the present specification disclose, in part, a vapor producing assembly. A vapor producing assembly disclosed herein comprises a permeation valve and a fluid chamber assembly. A vapor producing assembly disclosed herein may optionally comprise a control switch assembly. In one embodiment, a vapor producing assembly disclosed herein comprises a permeation valve and a fluid chamber assembly, but not a control switch assembly. In another embodiment, a vapor producing assembly disclosed herein comprises a permeation valve, a control switch assembly, and a fluid chamber assembly.

Figure 3A:
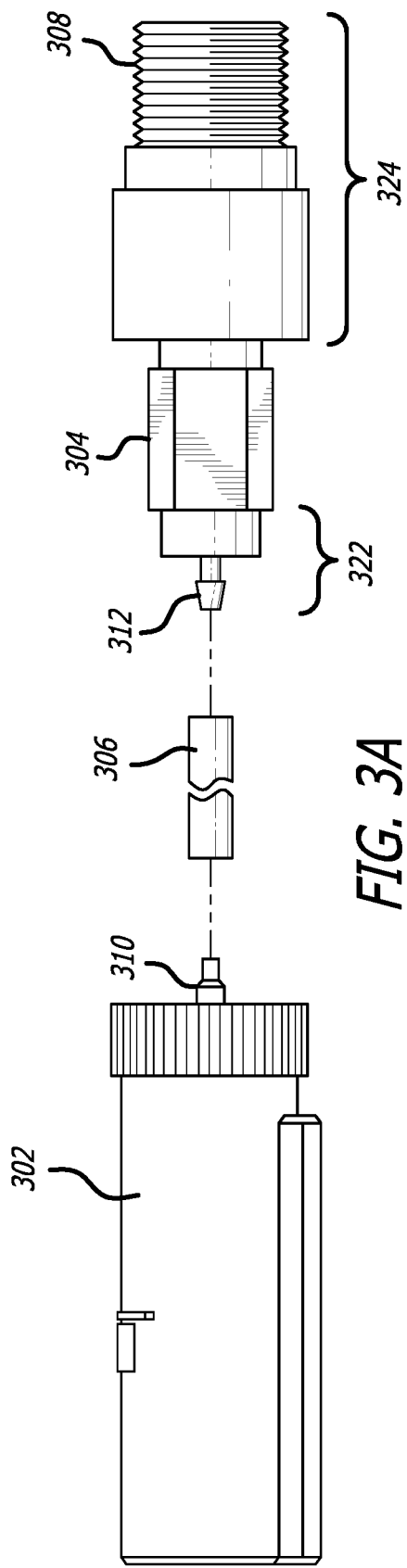
FIG. 3A illustrates an exemplary permeation valve and fluid chamber configuration.

In one embodiment, as illustrated in FIG. 3A, fluid chamber assembly 302 can be connected to permeation valve 304 using tube 306. A compressed gas cartridge (not illustrated) can be attached to permeation valve 304 a thread attachment point 308. First barb connector 310 and second barb connector 312 can be used to connect each component to tub 306. Tube 306 can be formed of any suitable material, e.g., plastic or metal. Also, tube 306 can be connected to barbs or other locking type connections using gaskets or o-rings. In other embodiments, the tube can simply be welded or attached to the components directly without the use of barbs.

Figure 3B:
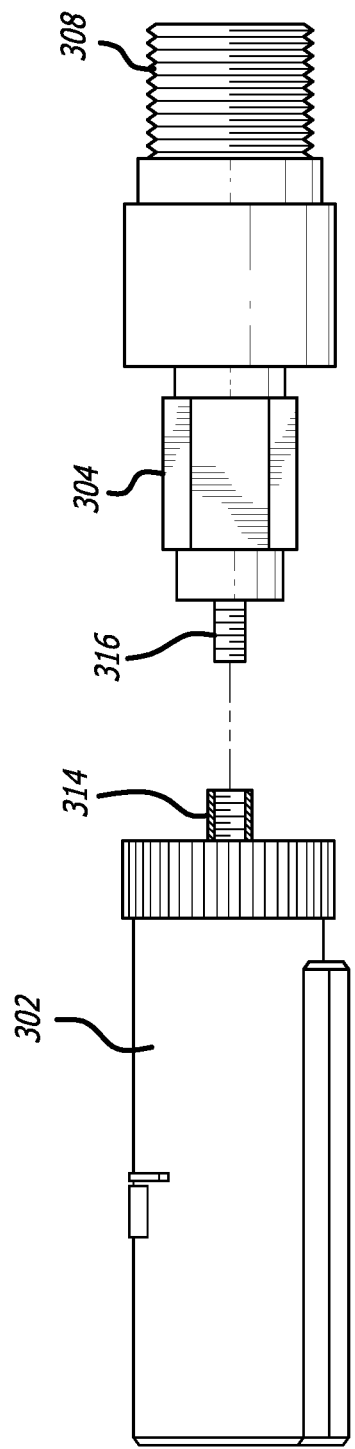
FIG. 3B illustrates another exemplary permeation valve and fluid chamber configuration.

As illustrated in FIG. 3B, fluid chamber assembly 302 and permeation valve 304 can be directly connected without the use of a tube. Here, male thread 314 on fluid chamber assembly 302 can be threaded over female thread 316 on permeation valve 304. The opposite thread configuration can also be used. In still other embodiments, fluid chamber assembly 302 and permeation valve 304 can be manufactured as a single piece with no need to manual attachment.

Figure 3C:
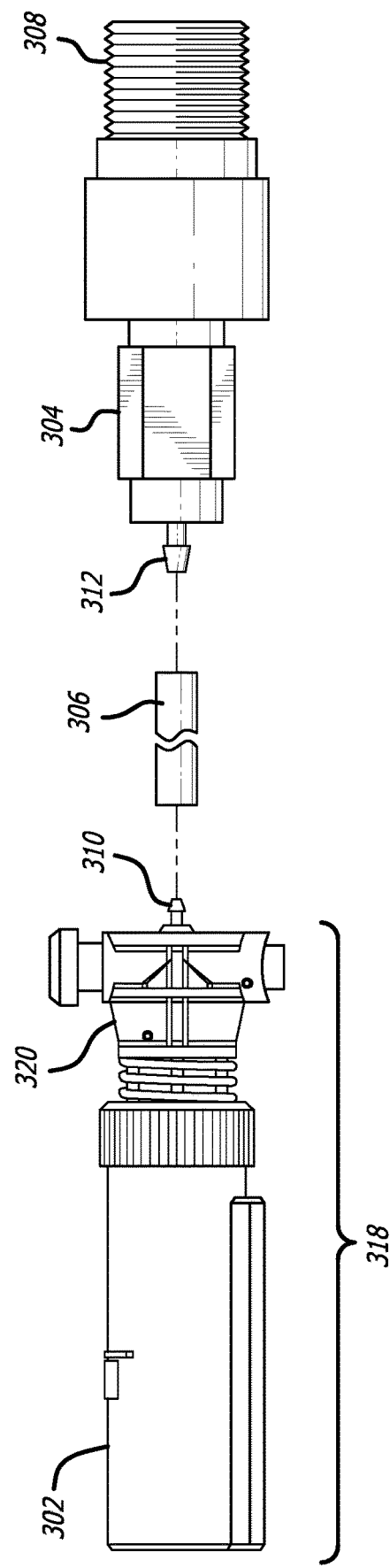
FIG. 3C illustrates yet another exemplary permeation valve and fluid chamber configuration including an actuator assembly.

FIG. 3C illustrates a system including vapor producing assembly 318 comprising fluid chamber assembly 302 and control switch assembly 320 connected to permeation valve 304 as in FIG. 3A. Control switch assembly 320 is an optional feature that may or may not be used with the devices described herein.

As illustrated in FIG. 3A, permeation valve 304 can be directly associated with two components. First connection apparatus 322 is typically threaded to permeation valve 304 and is used to associate it with fluid chamber assembly 302 and eventually a delivery area. Second connection apparatus 324 also threads onto permeation valve 304 and is typically used to interface permeation valve 304 with a compressed gas cylinder.

In one embodiment, as shown in FIGS. 4A-C, transdermal delivery device 400 comprises a housing 402 with leg stand 404 and fluid chamber access covering 406. Fluid chamber assembly access covering 406 is opened to shown open-ended delivery outlet 408 and fluid chamber assembly 410. Fluid chamber assembly access covering has track and grove arrangement 412 with housing 402 allowing the access covering 406 to slide back and forth. In other embodiment, hinge 414 can allow access covering 406 to swing upward to reveal open-ended delivery outlet 408 and fluid chamber assembly 410.

Cartridge retaining container 416 can be detached from transdermal delivery device 400 to expose the front end of permeation valve 418 where lance 420 is located. Cartridge retaining container 416 can hold compressed gas cartridge 422. Cartridge retaining container (not shown) has a threaded portion that can be screwed onto or off of a threaded portion of the external body shell 320.

In some embodiments, fluid chamber assembly access covering 406 can have a window 424 which when fluid chamber assembly access covering 406 is closed can be used to view the contents of fluid chamber 426. In such an embodiment, at least part of fluid chamber 426 adjacent to window 424 can be transparent.

Figure 6:
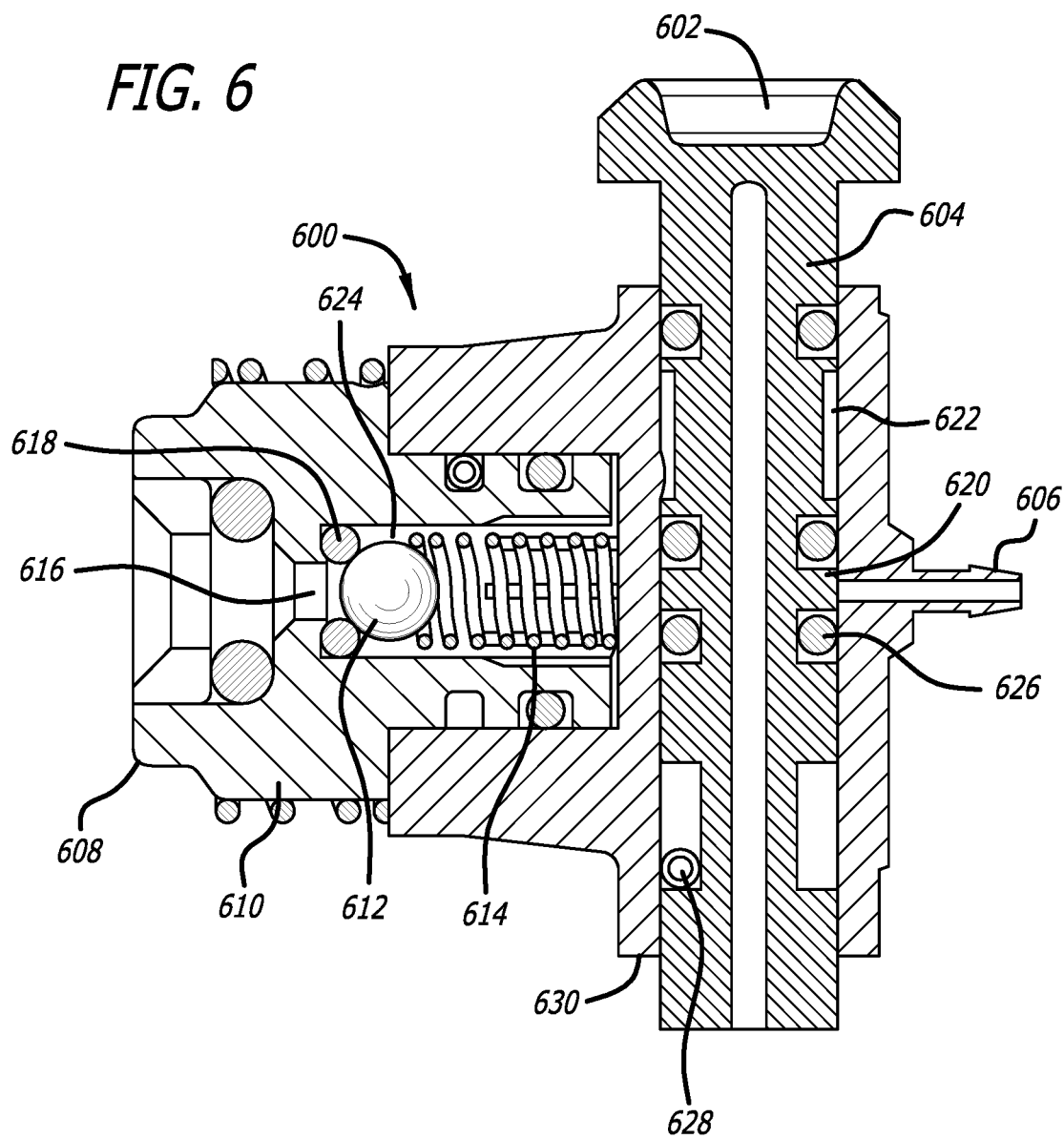
FIG. 6 illustrates a cross-section view of an exemplary control switch assembly.

FIG. 3C is a cross-sectional view of an alternative transdermal delivery device 428 comprising the additional component, a control switch 430 which may be the control switch assembly described in FIG. 6, or be one of a different design, but of similar function. Control switch 430 allows control of the instant of therapeutic agent delivery or duration of delivery. This is in contrast to a device without control switch 430 that would bleed the contents of cartridge 422 until depletion. In other words, control switch 430 allows the device to be turned on and off.

A permeation valve as disclosed herein comprises at least one permeation member. A permeation valve disclosed herein is designed to reduce the pressure of a gas coming from a compressed gas cartridge. In some instances, the permeation valve can increase the temperature of the gas so that when it enters into a fluid chamber assembly as disclosed here the gas will dissolve. A permeation valve disclosed herein can comprise a permeation member as well as a lance. The valve itself can be formed of a metal alloy, high strength glass reinforced nylon, or other lightweight material that can withstand the high pressure and cold temperature exerted by the gas as it leaves the compressed gas cartridge. A permeation valve disclosed herein can further include an adaptor to connect it to other portions of the device assembly. Exemplary permeation valves useful to operate the transdermal delivery device disclosed herein are described in, e.g., Hollars, Compressed Gas Cartridge permeation Dispenser having a Predictable Permeation Rate, U.S. Pat. No. 7,857,167, which is hereby incorporated by reference in its entirety for all that it discloses regarding permeation valves.

In one embodiment, a permeation valve disclosed herein can be set to reduce the pressure of a compressed gas to below about 40 psi (about 275 kPa) at 21.1° C. In aspects of this embodiment, a permeation valve can be set to reduce the pressure of a compressed gas to, e.g., about 35 psi (about 241 kPa), about 30 psi (about 207 kPa), about 25 psi (about 172 kPa), about 20 psi (about 138 kPa), or about 15 psi (about 103 kPa). In other aspects of this embodiment, a permeation valve can be set to reduce the pressure of a compressed gas to, e.g., below 40 psi (about 275 kPa), below 35 psi (about 241 kPa), below 30 psi (about 207 kPa), below 25 psi (about 172 kPa), below 20 psi (about 138 kPa), or below 15 psi (about 103 kPa). In yet other aspects of this embodiment, a permeation valve can be set to reduce the pressure of a compressed gas to between, e.g., about 15 psi (about 103 kPa) to about 40 psi (about 275 kPa), about 15 psi (about 103 kPa) to about 35 psi (about 241 kPa), about 15 psi (about 103 kPa) to about 30 psi (about 207 kPa), about 15 psi (about 103 kPa) to about 25 psi (about 172 kPa), or about 15 psi (about 103 kPa) to about 20 psi (about 138 kPa).

In another embodiment, a permeation valve disclosed herein increases the temperature of a compressed gas so that when the gas travels through a permeation valve and enters a fluid chamber assembly, the gas will not freeze a liquid contained in the fluid chamber assembly. In aspects of this embodiment, a permeation valve can increase the temperature of a compressed gas to, e.g., about 0° C., about 2° C., about 4° C., about 5° C., about 8° C., about 10° C., about 12° C., about 15° C., about 18° C., about 20° C., or about 22° C. In other aspects of this embodiment, a permeation valve can increase the temperature of a compressed gas to, e.g., at least 0° C., at least 2° C., at least 5° C., at least 8° C., at least 10° C., at least 12° C., at least 15° C., at least 18° C., at least 20° C., or at least 22° C. In yet other aspects of this embodiment, a permeation valve can increase the temperature of a compressed gas to between, e.g., about 0° C. to about 22° C., about 2° C. to about 22° C., about 4° C. to about 22° C., about 8° C. to about 22° C., about 12° C. to about 22° C., about 0° C. to about 18° C., about 2° C. to about 18° C., about 4° C. to about 18° C., about 8° C. to about 18° C., or about 12° C. to about 18° C.

In another embodiment, a permeation valve disclosed herein can be set to reduce the pressure of a compressed gas to about 15 psi (about 103 kPa) to about 40 psi (about 275 kPa) and increase the temperature of the compressed gas to about 0° C. to about 22° C. In another embodiment, a permeation valve disclosed herein can be set to reduce the pressure of a compressed gas to about 15 psi (about 103 kPa) to about 40 psi (about 275 kPa) and increase the temperature of the compressed gas to about 4° C. to about 22° C. In another embodiment, a permeation valve disclosed herein can be set to reduce the pressure of a compressed gas to about 15 psi (about 103 kPa) to about 40 psi (about 275 kPa) and increase the temperature of the compressed gas to about 8° C. to about 22° C. In another embodiment, a permeation valve disclosed herein can be set to reduce the pressure of a compressed gas to about 15 psi (about 103 kPa) to about 40 psi (about 275 kPa) and increase the temperature of the compressed gas to about 12° C. to about 22° C.

In another embodiment, a permeation valve disclosed herein can be set to reduce the pressure of a compressed gas to below about 40 psi (about 275 kPa) and increase the temperature of the compressed gas to at least 0° C. In another embodiment, a permeation valve disclosed herein can be set to reduce the pressure of a compressed gas to below about 40 psi (about 275 kPa) and increase the temperature of the compressed gas to at least 4° C. In another embodiment, a permeation valve disclosed herein can be set to reduce the pressure of a compressed gas to below about 40 psi (about 275 kPa) and increase the temperature of the compressed gas to at least 8° C. In another embodiment, a permeation valve disclosed herein can be set to reduce the pressure of a compressed gas to below about 40 psi (about 275 kPa) and increase the temperature of the compressed gas to at least 12° C.

Figure 5A:
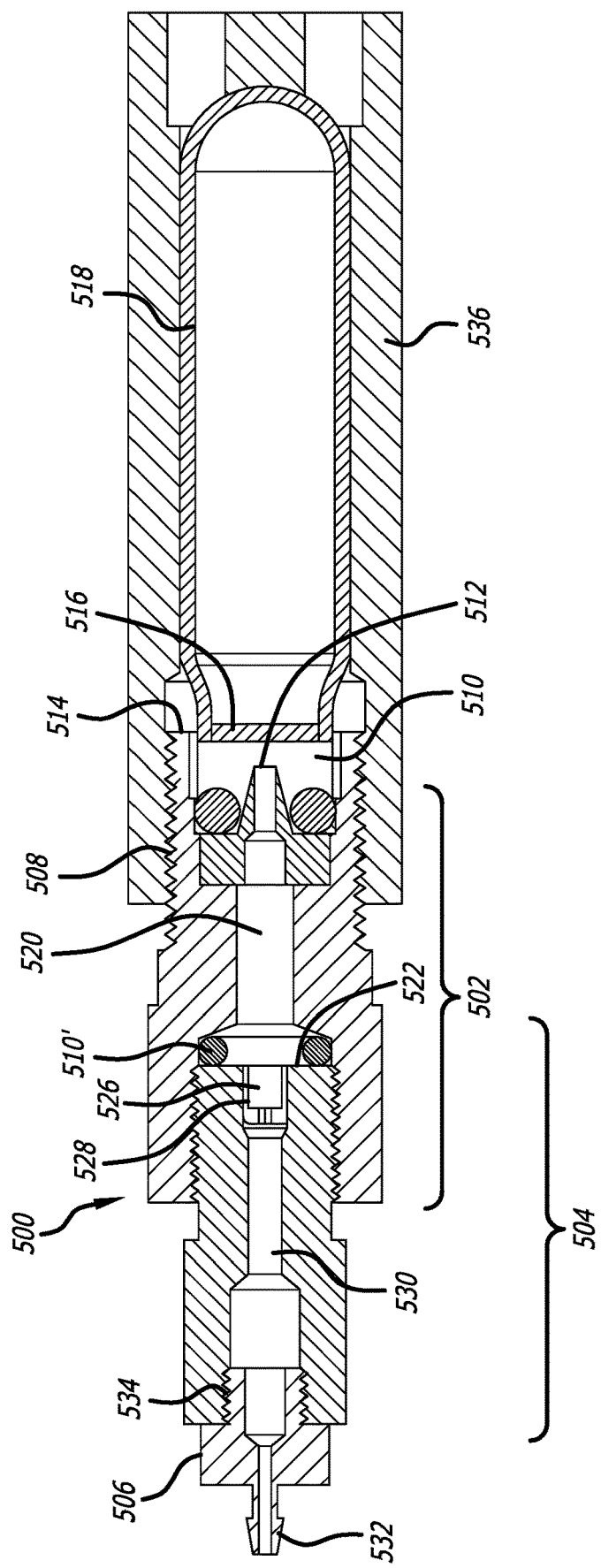
FIG. 5A illustrates a cross-section view of an exemplary permeation valve with gas cartridge not fully engaged with a piercing member.
Figure 5B:
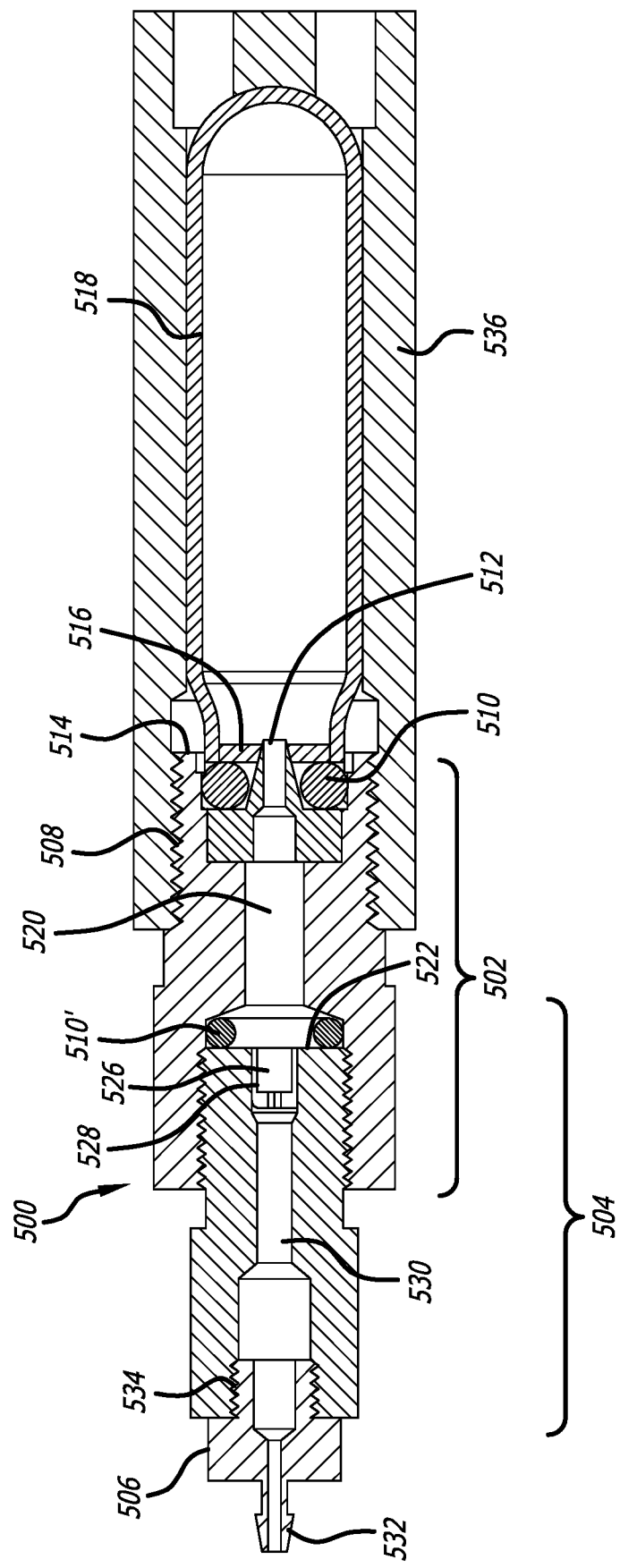
FIG. 5B illustrates gas cartridge engaged with piercing member.

In one embodiment, as shown in FIGS. 5A and 5B, permeation valve assembly 500 comprises lance housing 502, permeation member housing 504, first attachment member 506 and second attachment member 508. In some embodiments, each of the above members can be formed as one single unit, and in other embodiments, the members can be separate and connectable. Connection points can be sealed using o-rings 510, 510' or other means such as gaskets, barbs, or compression fittings.

Lance housing 502 can include lance 512 located at upstream end 514 of permeation valve assembly 500. Lance 512 can puncture a compressed gas cartridge seal 516 located on the neck of the compressed gas cartridge 518 when the same is brought into contact with lance 512. A lance as disclosed herein may be of any design that can pierce the seal of a compressed gas cartridge and allows release of compressed gas from the cartridge into permeation valve assembly 500 in a manner that ensures proper operation of the transdermal delivery device. Such a lance design includes, e.g., a hollow piercing lance design and solid piercing lance design.

As illustrated in FIG. 5A, compressed gas cartridge 518 can be threaded onto second attachment member 508. However, until compressed gas cartridge seal 516 reaches lance 512 as illustrated in FIG. 5B, compressed gas cartridge 518 can remain sealed. Once lance 512 punctures compressed gas cartridge seal 516 gas can exit the cartridge and proceed through the device.

As air exits compressed gas cartridge 518, it either passes through a hollow lance, around a lance member or both, and proceeds through the device. Generally, lance 512, may not substantially impeded airflow or regulate air pressure. Then, high pressure air can travel through lance housing 502 down interior bore 520 until it reaches face 522 of permeation member housing 504. At face 522, the high pressure air enters permeation member housing 504 through a hole of face 522. Just inside this hole the high pressure air encounters a permeation member 526. Permeation member 526 can make a seal with surrounding wall 528.

A purpose of permeation member 526 can be to adjust and/or reduce air pressure. For example, air entering permeation member housing 504 can be at a high pressure and air eventually exiting permeation member housing 504 on the opposite side can be of a lower pressure. Permeation member 526 can be composed of any material that is semi-permeable such as from a family of rubber, cork, textile materials, porous polymeric materials, densely sintered metal, or any other suitable material that provides an appropriate and/or desired permeation rate.

Air gradually permeates through permeation member 526 at a rate characteristic of the material used to form the member. As permeated air exits permeation member 526 it is at a lower pressure than when it entered. This lower pressure air can then travel through permeation housing bore 530 and can flow freely through the remainder of permeation valve assembly 500.

Permeation member can also be in the form of an o-ring seal or other functional part of the device instead or in addition to a standalone permeation member. For example, a permeation member or other components of a permeation valve as described in U.S. Pat. No. 7,857,167 are hereby incorporated entirely by reference for all that is disclosed about permeation valves.

First attachment member 506 and second attachment member 508 can be the same or different depending on the needs and configuration of the device. In FIGS. 5A and 5B, first attachment member 506 is a barb connector 532 threaded onto permeation member housing 504 at threat attachment 534. Also in FIGS. 5A and 5B, second attachment member 508 is a threaded attachment for an opposite threaded cartridge retaining container 536. In another embodiment, a cartridge retaining container 536 is not needed. There, compressed gas cartridge 518 can screw directly onto second attachment member 508 because it is threaded.

In some embodiments, permeation valve assembly 500 can include no moving and/or mechanical parts (e.g. springs, actuators or moving bearings). In such embodiments, permeation is controlled entirely by permeation member 526. This control in some cases can increase the safety of the device and prevent otherwise unwanted mechanical problems and can also increase the simplicity and reduce the overall size of a device.

A permeation valve assembly can be configured (e.g. with a permeation member and/or orifice size) to dispense a gas for an appropriate amount of time to ensure an appropriate amount of gas is dissolvent into the liquid. In one embodiment, the permeation valve assembly can be adjusted to dispense a gas for, e.g., about 3 minutes, about 5 minutes, about 7 minutes, about 10 minutes, about 12 minutes, about 15 minutes, about 18 minutes, or about 20 minutes. In another embodiment, the permeation valve assembly can be adjusted to dispense a gas for, e.g., at least 3 minutes, at least 5 minutes, at least 7 minutes, at least 10 minutes, at least 12 minutes, at least 15 minutes, at least 18 minutes, or at least 20 minutes. In yet another embodiment, the permeation valve assembly can be adjusted to dispense a gas for, e.g., about 3 minutes to about 5 minutes, about 3 minutes to about 10 minutes, about 3 minutes to about 15 minutes, about 3 minutes to about 20 minutes, about 5 minutes to about 10 minutes, about 5 minutes to about 15 minutes, or about 5 minutes to about 20 minutes.

In some embodiments, once a compressed gas cylinder is threaded onto a permeation valve assembly and punctured by a lance, the permeation of gas through the permeation member is constant until the compressed gas is depleted from the cylinder. In other words, once the compressed gas cylinder is lanced, gas begins to flow without interruption until depleted with no "off" valve.

In other embodiments, a compressed gas cylinder can be provided that is permanently and/or non-removably attached to a device. In such an embodiment, a button can be used to lance the cylinder at a given time and the cylinder can be used to completion. Upon depletion of the gas, the device can be discarded. Such an embodiment can be used as a single use device. A patient may receive a batch of devices, each to be used once and discarded.

In other embodiments, a control switch assembly can be inserted between the permeation valve assembly and the fluid chamber to potentially and/or optionally to stop the gas flow before the gas cylinder is depleted. Such a control switch as disclosed herein can comprise an actuator, a switch body, an inlet port and an outlet port and may operate by a mechanical or an electronic design. A control switch assembly disclosed herein is designed to control when low pressure gas leaving the regulator assembly is allowed to enter into the fluid chamber assembly.

In one embodiment, as shown in FIG. 6, control switch assembly 600 comprises actuator 602, switch body 604, inlet port 606, flow ball seat valve 608, and flow valve insert 610. Inlet port 606 can in communication with an outlet port of a permeation valve disclosed herein. However, actuator 602 can prevent passage of the gas into flow ball seat valve 608. Upon activation of actuator 602, a channel is formed that establishes communication between inlet port 606 and flow ball seat valve 608, thereby enabling gas to enter into flow ball seat valve 608. Flow ball seat valve 608 comprises ball seat valve body 610, housing seat valve ball 612, ball spring 614, and ball seat valve outlet port 616. Activation of actuator 602 releases tension in ball spring 614 which reduces pressure on ball 612 forced against o-ring 618 by the tension of ball spring 614. As actuator 602 is depressed, a plugged portion 620 is moved down and an open portion 622 is revealed connecting inlet port 606 and ball chamber 624 wherein the pressure can effectuate housing seat valve ball 612. Plugged portion 620 and open portion 622 are differentiated by one or more o-rings 626. Actuator 602 can be locked in the "open" position when depressed using a locking mechanism 628 that engages with bottom portion 630. With pressure removed, gas can flow through the flow ball seat valve 608, exiting via ball seat valve outlet port 616. A channel in communication with control switch assembly 600 and a fluid chamber assembly disclosed herein allows gas to flow into the fluid chamber assembly. This communication channel can be formed by an inlet port of a fluid chamber assembly as disclosed herein and flow valve insert 610.

A fluid chamber assembly disclosed herein comprises a fluid container, and inlet port and an outlet port. The fluid container can hold the liquid that will be supersaturated by the gas entering into the chamber from a pressure-temperature regulator assembly. The liquid can be water, a physiologically buffered solution, or any other suitable liquid. A suitable liquid is one that 1) allows for an appropriate amount of gas to be dissolved into the liquid in order to produce a vapor comprising liquid particles including a supersaturated amount of a therapeutic agent; and 2) maintains, enables, or ensures the activity of a therapeutic agent, thereby ensuring that a therapeutically effective amount of the agent is received by an individual upon administration. For example, carbon dioxide exits in a gaseous form and a molecular form. It is the molecular form of carbon dioxide that is capable of dissolving in a liquid, such as, e.g., water, which allows for the easily absorbed of carbon dioxide through the skin. Conversely, at higher pH, carbon dioxide tends to change to carbonic acid ($H_2CO_3$) and bicarbonate ions which are not easily absorbed through the skin. The lower the pH of the liquid, the more molecular carbon dioxide exists. As such, when the gas is carbon dioxide, the pH of the liquid should be slightly acidic, such as, e.g., no more then about pH 6, no more then about pH 5.5, no more then about pH 5, no more then about pH 4.5, or no more then about pH 4.

Alternatively, another substance capable of dissolving a supersaturated amount of gas may be used instead of a liquid. Non-limiting examples of such a substance include colloids, such as, e.g., foams, liquid aerosols, emulsions, gels, and sols.

A liquid disclosed herein comprises a therapeutic agent. As used herein, the term "therapeutic agent" is synonymous with "active ingredient" and refers to used to any substance that provides a beneficial effect to an individual being administered the therapeutic agent.

One type of therapeutic agent is the gas that has been dissolved into the liquid as disclosed herein. An exemplary gas that is a therapeutic agent is carbon dioxide. Current uses of gases in medicine are rapidly being explored because these molecules are important biological messengers. For example, increasing the level of carbon dioxide in the blood decreases the pH due to the conversion of carbon dioxide into bicarbonate. This decreased pH enables oxygen to more readily dissociate from hemoglobin, referred to as the "Bohr effect." Additionally, an increased level of carbon dioxide improves circulation and blood flow by triggering the release vasodilatory agents which dilate blood vessels in an effort to increase oxygen supply. As such, increasing carbon dioxide level increases tissue oxygen which, in turn, increases dilation of blood vessels which allows for the delivery of more nutrients to cells, and increasing higher oxygen supply to cells thereby enhancing cellular metabolism. As such, increasing the level of tissue oxygen in this manner provides many beneficial effects that promote skin health including, without limitation, promoting wound healing, improving skin texture, and providing anti-aging effects.

Another type of therapeutic agent that can be administered by a transdermal delivery device disclosed herein is a drug that can either be dissolved in a liquid disclosed herein or become part of the vapor upon vaporization. Approximately half of the pharmaceutical drugs available on the market today possess a molecular affinity for water. This affinity manifests itself in a tendency to dissolve in, mix with, or absorb water. Therapeutic agents with these characteristics are referred to as hydrophilic therapeutic agents and comprise small molecule or chemical drugs as well a biologics. Hydrophilic therapeutic agents include, without limitation, nicotine antihistamines, β-blockers, calcium channel blockers, non-steroidal anti-inflammatory drugs, contraceptives, anti-arrhythmic drugs, insulin, antivirals, pain medications, hormones, α-interferon, vitamins (e.g., vitamin D), and chemotherapeutic agents. In one embodiment, the drug includes one or more water-soluble medications.

Another type of therapeutic agent that can be administered by a transdermal delivery device disclosed herein is a vitamin that can either be dissolved in a liquid disclosed herein or become part of the liquid particle upon vaporization.

In one embodiment, the amount of gas dissolved in the liquid is, e.g., about 30,000 ppm, about 35,000 ppm, about 40,000 ppm, about 45,000 ppm, about 50,000 ppm, about 55,000 ppm, or about 60,000 ppm. In another embodiment, the amount of gas dissolved in the liquid is, e.g., at least 30,000 ppm, at least 35,000 ppm, at least 40,000 ppm, at least 45,000 ppm, at least 50,000 ppm, at least 55,000 ppm, or at least 60,000 ppm. In yet another embodiment, the amount of gas dissolved in the liquid is, e.g., at most 30,000 ppm, at most 35,000 ppm, at most 40,000 ppm, at most 45,000 ppm, at most 50,000 ppm, at most 55,000 ppm, or at most 60,000 ppm. In still another embodiment, the amount of gas dissolved in the liquid is between, e.g., about 30,000 ppm to about 35,000 ppm, about 30,000 ppm to about 40,000 ppm, about 30,000 ppm to about 45,000 ppm, about 30,000 ppm to about 50,000 ppm, about 35,000 ppm to about 40,000 ppm, about 35,000 ppm to about 45,000 ppm, about 35,000 ppm to about 50,000 ppm, about 40,000 ppm to about 45,000 ppm, about 40,000 ppm to about 50,000 ppm, or about 50,000 ppm to about 60,000 ppm.

In an embodiment where the therapeutic agent is not or may not be the dissolved gas, the agent can be contained in the liquid placed in the fluid container. Additionally, a liquid placed into the fluid container may comprise both the additional therapeutic agent as well as a dissolved gas that also provides a therapeutic effect.

A fluid chamber assembly may optionally comprise a fluid container cap that detachably engages a fluid container disclosed herein. The ability to detach a fluid container as disclosed herein allows for the refilling of a liquid as needed. For example, in an application involving the treatment of a wound, the liquid may contain both a wound healing drug like cyclosporine as well as dissolved molecular carbon dioxide.

An inlet port as disclosed herein is designed to receive the low pressure gas flowing from the permeation valve and channels the gas into the fluid chamber assembly. Once in the fluid chamber assembly, the gas will dissolve into the liquid contained in the fluid container to produce a liquid comprising a supersaturated amount of dissolved gas molecules. As used herein, the term "supersaturated" when used in reference to "supersaturated amount of dissolved gas molecules" refers to a liquid disclosed herein that contains more of a dissolved gas than the liquid can accommodate under ambient temperature and air pressure, typically measured at 25° C. and 1 atm. For example, with reference to a transdermal delivery device disclosed herein, the pressure of dissolved gas in the fluid chamber assembly is greater than the pressure of the gas outside the assembly. In one embodiment, an inlet port as disclosed herein comprises a check value, a spring and a poppet.

An outlet port as disclosed herein is designed to release a vapor including a supersaturated amount of dissolved gas molecules and/or a therapeutic agent at ambient pressure from the fluid chamber assembly into an open-ended delivery outlet where it can be administered to an individual. In one embodiment, an outlet port as disclosed herein comprises a check value, a spring and a poppet. Vaporization of the liquid comprising a supersaturated amount of dissolved gas is achieved when the pressure inside the liquid container is sufficient to expel the liquid through the outlet port. In aspects of this embodiment, vaporization of the liquid comprising a supersaturated amount of dissolved gas is achieved when the pressure inside the liquid container is, e.g., about 15 psi, about 20 psi, about 25 psi, about 30 psi, about 35 psi, about 40 psi, about 45 psi, or about 50 psi. In other aspects of this embodiment, vaporization of the liquid comprising a supersaturated amount of dissolved gas is achieved when the pressure inside the liquid container is, e.g., at least 15 psi, at least 20 psi, at least 25 psi, at least 30 psi, at least 35 psi, at least 40 psi, at least 45 psi, or at least 50 psi. In yet other aspects of this embodiment, vaporization of the liquid comprising a supersaturated amount of dissolved gas is achieved when the pressure inside the liquid container is, e.g., at most 15 psi, at most 20 psi, at most 25 psi, at most 30 psi, at most 35 psi, at most 40 psi, at most 45 psi, or at most 50 psi. In still other aspects of this embodiment, vaporization of the liquid comprising a supersaturated amount of dissolved gas is achieved when the pressure inside the liquid container is from, e.g., about 15 psi to about 50 psi, about 20 psi to about 50 psi, about 25 psi to about 50 psi, about 30 psi to about 50 psi, about 35 psi to about 50 psi, about 15 psi to about 45 psi, about 20 psi to about 45 psi, about 25 psi to about 45 psi, about 30 psi to about 45 psi, about 35 psi to about 45 psi, about 15 psi to about 40 psi, about 20 psi to about 40 psi, about 25 psi to about 40 psi, about 30 psi to about 40 psi, about 15 psi to about 35 psi, about 20 psi to about 35 psi, about 25 psi to about 35 psi, about 15 psi to about 30 psi, or about 20 psi to about 30 psi.

A vapor as disclosed herein can comprise liquid particles and a supersaturated amount of dissolved gas molecules. A vapor can be a solution comprising a liquid and a gas, or a liquid aerosol, which is a colloid composition comprising a liquid and a gas. When the therapeutic agent is not the dissolved gas, a vapor also comprises a therapeutic agent as disclosed herein.

Vaporization can create liquid particles having an average size small enough to be able to enter the pores of the skin. In one embodiment, the average size of a liquid particle can be, e.g., about 100 μm, about 75 μm, about 50 μm, or about 25 μm. In another embodiment, the average size of a liquid particle is, e.g., no more than 100 μm, no more than 75 μm, no more than 50 μm, or no more than 25 μm. In yet another embodiment, the average size of a liquid particle can be, e.g., about 1 μm to about 100 μm, about 1 μm to about 75 μm, about 1 μm to about 50 μm, about 1 μm to about 25 μm, about 5 μm to about 100 μm, about 5 μm to about 75 μm, about 5 μm to about 50 μm, about 5 μm to about 25 μm, about 10 μm to about 100 μm, about 10 μm to about 75 μm, about 10 μm to about 50 μm, or about 10 μm to about 25 μm.

A fluid chamber assembly may optionally comprise a pressure relief valve as a safety measure for avoiding an over-pressurization of the vapor producing assembly or component thereof. In one embodiment, a pressure relief valve is, e.g., a 30 psi valve, a 35 psi valve, a 40 psi valve, a 45 psi valve, or a 50 psi valve. In other embodiments, a pressure relief valve may not be needed because the permeation valve is non-mechanical and provides a predetermined, constant gas flow/pressure to the fluid chamber.

A fluid chamber assembly may optionally comprise a baffle assembly comprising one or more conical baffles or mixing elements. The baffle assembly is connected to the fluid container or fluid container cap. The baffles are positioned in a column configuration with each baffle above and partially overlapping the other and their circular base sides face away from the inlet port. Narrow connecting pieces at the periphery of this column position the baffles in place. As low pressure gas enters into the fluid container via the inlet port, the gas flows pass over the baffles to enhance the mixing of the gas and liquid. As such, the baffles are designed to speed up and/or increase the amount of gas dissolved into the liquid. In one embodiment, fluid chamber assembly does not comprise a baffle assembly.

Figure 7:
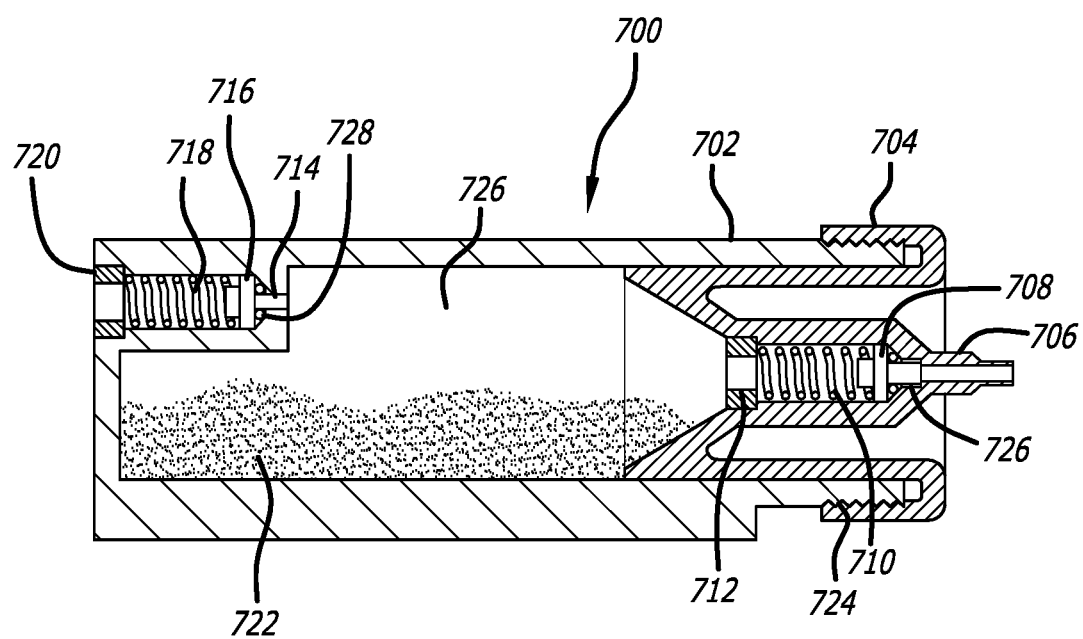
FIG. 7 illustrates a cross-section view of an exemplary fluid chamber assembly.

In one embodiment, as shown in FIG. 7, fluid chamber assembly 700 comprises fluid container 702, fluid container cap 704 containing inlet port 706 including inlet poppet 708, inlet spring 710 and inlet check value 712, and outlet port 714 including outlet poppet 716, outlet spring 718 and outlet check value 720. Liquid 722 as disclosed herein is placed into fluid container 702 and attached to fluid container cap 704 via threads 724. Threads are used for non-limiting illustration purposes and can be replaced by any securing means known in the art. Gas enters fluid chamber assembly 700 via inlet port 706 where the gas pressure moves inlet poppet 708 against inlet spring 710 until the seal between inlet poppet 708 and inlet face 726 is broken and gas can enter chamber 726 and dissolve into liquid 722. After a predetermined period of time or after a certain or predetermined amount of pressure has built, the liquid comprising a supersaturated amount of gas dissolved gas can be released when pressure has overcome the force of outlet spring 718 on outlet poppet 716 and the seal is broken between outlet poppet 716 and outlet port face 728 sealed with an o-ring. After the seal is broken, gas can escape as a vapor.

Aspects of the present specification disclose, in part, a method of producing a substance comprising a supersaturated amount of dissolved gas. As used herein, the term "substance" includes any material capable of dissolving a supersaturated amount of gas. Non-limiting examples of a substance include liquids and colloids, such as, e.g., foams, liquid aerosols, emulsions, gels, and sols. In the method disclosed herein, a substance is placed in an air-tight container and the substance is then exposed to a gas. Upon such exposure, the gas dissolves into the substance in an amount greater than the substance could dissolve at 25° C. and 1 atm. The resulting substance supersaturated with the dissolved gas can then be administered to an individual to treat a condition as disclosed herein.

In one embodiment, the amount of gas dissolved in the substance can be, e.g., about 30,000 ppm, about 35,000 ppm, about 40,000 ppm, about 45,000 ppm, about 50,000 ppm, about 55,000 ppm, or about 60,000 ppm. In another embodiment, the amount of gas dissolved in the substance can be, e.g., at least 30,000 ppm, at least 35,000 ppm, at least 40,000 ppm, at least 45,000 ppm, at least 50,000 ppm, at least 55,000 ppm, or at least 60,000 ppm. In yet another embodiment, the amount of gas dissolved in the substance can be, e.g., at most 30,000 ppm, at most 35,000 ppm, at most 40,000 ppm, at most 45,000 ppm, at most 50,000 ppm, at most 55,000 ppm, or at most 60,000 ppm. In still another embodiment, the amount of gas dissolved in the substance can be between, e.g., about 30,000 ppm to about 35,000 ppm, about 30,000 ppm to about 40,000 ppm, about 30,000 ppm to about 45,000 ppm, about 30,000 ppm to about 50,000 ppm, about 35,000 ppm to about 40,000 ppm, about 35,000 ppm to about 45,000 ppm, about 35,000 ppm to about 50,000 ppm, about 40,000 ppm to about 45,000 ppm, about 40,000 ppm to about 50,000 ppm, or about 50,000 ppm to about 60,000 ppm.

In another embodiment, a method of producing a substance comprising a supersaturated amount of dissolved gas disclosed herein is performed using a transdermal delivery device disclosed herein. For example, a fluid chamber assembly can be filled with a liquid or a colloid as disclosed herein and the device activated to produce a liquid or a colloid comprising a supersaturated amount of dissolved gas.

Aspects of the present specification further disclose, in part, a method of transdermally administering a therapeutically effective amount of therapeutic agent disclosed herein. In one embodiment, the method disclosed herein comprises the step of administering a substance comprising a supersaturated amount of dissolved gas to an individual using a transdermal delivery device disclosed herein. Administration of the dissolved gas treats a symptom associate with a condition and is therefore a therapeutically effective amount. A substance may be a vapor, a liquid, a foam, a liquid aerosol, an emulsion, a gel, a sol, or other substance that can become supersaturated with an amount of dissolved gas. In an aspect of this embodiment, a substance comprising a supersaturated amount of dissolved gas is without another therapeutic agent. In another aspect of this embodiment, the dissolved gas is molecular carbon dioxide. In yet another aspect of this embodiment, the dissolved gas is molecular carbon dioxide, which also serves as the therapeutic agent.

In another embodiment, the method disclosed herein comprises the step of administering a substance comprising a supersaturated amount of dissolved gas and a therapeutic agent to an individual using a transdermal delivery device disclosed herein. Administration of the dissolved gas and/or the therapeutic agent treats a symptom associate with a condition and is therefore a therapeutically effective amount. A substance may be a vapor, a liquid, a foam, a liquid aerosol, an emulsion, a gel, a sol, or other substance that can become supersaturated with an amount of dissolved gas. In an aspect of this embodiment, the dissolved gas is molecular carbon dioxide. In another aspect of this embodiment, the dissolved gas is molecular carbon dioxide, which also serves as the therapeutic agent.

Aspects of the present specification disclose, in part, a method of treating a condition of an individual. In one embodiment, a method of treating a condition disclosed herein comprises the step of administering a composition comprising a substance including a therapeutically effective amount of dissolved gas using a transdermal delivery device as disclosed herein to the individual suffering from a condition, wherein the administration of the composition reduces a symptom associated with condition. Administration of the gas treats a symptom associate with the condition. A substance may be a vapor, a liquid, a foam, a liquid aerosol, an emulsion, a gel, a sol, or other substance that can become supersaturated with an amount of dissolved gas. In an aspect of this embodiment, a composition comprising a substance including a therapeutically effective amount of dissolved gas is without another therapeutic agent. In another aspect of this embodiment, the dissolved gas is molecular carbon dioxide. In yet another aspect of this embodiment, the dissolved gas is molecular carbon dioxide, which also serves as the therapeutic agent.

In another embodiment, a method of treating a condition disclosed herein comprises the step of administering a composition comprising a substance including a therapeutically effective amount of dissolved gas and a therapeutically effective amount of another therapeutic agent using a transdermal delivery device as disclosed herein to the individual suffering from a condition, wherein the administration of the composition reduces a symptom associated with condition. Administration of the gas and/or the therapeutic agent treats a symptom associate with a condition and is therefore a therapeutically effective amount. A substance may be a vapor, a liquid, a foam, a liquid aerosol, an emulsion, a gel, a sol, or other substance that can become supersaturated with an amount of dissolved gas. In an aspect of this embodiment, the dissolved gas is molecular carbon dioxide. In another aspect of this embodiment, the dissolved gas is molecular carbon dioxide, which also serves as the therapeutic agent.

As used herein, the term "treating," refers to reducing or eliminating in an individual a cosmetic or clinical symptom associated with a condition; or delaying or preventing in an individual the onset of a cosmetic or clinical symptom associated with a condition. For example, the term "treating" can mean reducing a symptom associated with a condition by, e.g., at least 20%, at least 30%, at least 40%, at least 50%, at least 60%, at least 70%, at least 80%, at least 90% or at least 100%. The effectiveness of a therapeutic agent disclosed herein in treating a condition can be determined by observing one or more cosmetic, clinical symptoms, and/or physiological indicators associated with the condition. An improvement in a condition also can be indicated by a reduced need for a concurrent therapy. Those of skill in the art will know the appropriate symptoms or indicators associated with specific condition and will know how to determine if an individual is a candidate for treatment with a therapeutic agent by using the transdermal delivery device disclosed herein.

Aspects of the present specification provide, in part, administering a therapeutically effective amount of a therapeutic agent disclosed herein. As used herein, the term "therapeutically effective amount" is synonymous with "therapeutically effective dose" and refers to the minimum dose of therapeutic agent disclosed herein necessary to achieve the desired therapeutic effect and includes a dose sufficient to reduce a symptom associated with a condition.

In aspects of this embodiment, a therapeutically effective amount of a therapeutic agent disclosed herein reduces a symptom associated with a condition by, e.g., at least 10%, at least 20%, at least 30%, at least 40%, at least 50%, at least 60%, at least 70%, at least 80%, at least 90% or at least 100%. In other aspects of this embodiment, a therapeutically effective amount of a therapeutic agent disclosed herein reduces a symptom associated with a condition by, e.g., at most 10%, at most 20%, at most 30%, at most 40%, at most 50%, at most 60%, at most 70%, at most 80%, at most 90% or at most 100%. In yet other aspects of this embodiment, a therapeutically effective amount of a therapeutic agent disclosed herein reduces a symptom associated with a condition by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In still other aspects of this embodiment, a therapeutically effective amount of a therapeutic agent disclosed herein is the dosage sufficient to reduces a symptom associated with a condition for, e.g., at least one week, at least one month, at least two months, at least three months, at least four months, at least five months, at least six months, at least seven months, at least eight months, at least nine months, at least ten months, at least eleven months, or at least twelve months.

The actual therapeutically effective amount of a therapeutic agent disclosed herein to be administered to an individual can be determined by a person of ordinary skill in the art by taking into account factors, including, without limitation, the type of condition, the location of the condition, the cause of the condition, the severity of the condition, the duration of treatment, the degree of relief desired, the duration of relief desired, the particular therapeutic agent used, the rate of excretion of the therapeutic agent used, the pharmacodynamics of the therapeutic agent used, the nature of the other compounds to be included in the vapor, the particular characteristics, history and risk factors of the individual, such as, e.g., age, weight, general health and the like, the response of the individual to the treatment, or any combination thereof. A therapeutically effective amount of a therapeutic agent disclosed herein can thus readily be determined by the person of ordinary skill in the art considering all criteria and utilizing his best judgment on the individual's behalf.

With reference to carbon dioxide as the therapeutic agent, 600 ppm of dissolved molecular carbon dioxide is the minimum amount necessary to produce a therapeutic effect. This equates to 600 parts of carbon dioxide mixed with one million parts of water, or about 0.6% carbon dioxide and 99.4% water. In aspects of this embodiment, a therapeutically effective amount of a dissolved molecular $CO_2$ therapeutic agent disclosed herein can be, e.g., about 600 ppm, about 700 ppm, about 800 ppm, about 900 ppm, about 1,000 ppm, about 1,500 ppm, about 2,000 ppm, about 2,500 ppm, about 3,000 ppm, about 3,500 ppm, about 4,000 ppm, about 4,500 ppm, about 5,000 ppm, about 5,500 ppm, or about 6,000 ppm. In other aspects of this embodiment, a therapeutically effective amount of a dissolved molecular carbon dioxide therapeutic agent disclosed herein can be, e.g., at least 600 ppm, at least 700 ppm, at least 800 ppm, at least 900 ppm, at least 1,000 ppm, at least 1,500 ppm, at least 2,000 ppm, at least 2,500 ppm, at least 3,000 ppm, at least 3,500 ppm, at least 4,000 ppm, at least 4,500 ppm, at least 5,000 ppm, at least 5,500 ppm, or at least 6,000 ppm. In other aspects of this embodiment, a therapeutically effective amount of a dissolved molecular carbon dioxide therapeutic agent disclosed herein can be between, e.g., about 600 ppm to about 1,000 ppm, about 600 ppm to about 2,000 ppm, about 600 ppm to about 3,000 ppm, about 600 ppm to about 4,000 ppm, about 600 ppm to about 5,000 ppm, about 600 ppm to about 6,000 ppm, about 600 ppm to about 10,000 ppm, about 600 ppm to about 20,000 ppm, about 600 ppm to about 30,000 ppm, about 600 ppm to about 40,000 ppm, about 600 ppm to about 50,000 ppm, about 600 ppm to about 60,000 ppm, about 1,000 ppm to about 2,000 ppm, about 1,000 ppm to about 3,000 ppm, about 1,000 ppm to about 4,000 ppm, about 1,000 ppm to about 5,000 ppm, about 1,000 ppm to about 6,000 ppm, about 1,000 ppm to about 10,000 ppm, about 1,000 ppm to about 20,000 ppm, about 1,000 ppm to about 30,000 ppm, about 1,000 ppm to about 40,000 ppm, about 1,000 ppm to about 50,000 ppm, or about 1,000 ppm to about 60,000 ppm.

In an embodiment, a therapeutically effective amount of a molecular carbon dioxide increased blood flow. In aspects of this embodiment, a therapeutically effective amount of a molecular carbon dioxide increases blood flow by, e.g., at least 10%, at least 20%, at least 30%, at least 40%, at least 50%, at least 60%, at least 70%, at least 80%, at least 90% or at least 100%. In other aspects of this embodiment, a therapeutically effective amount of a molecular carbon dioxide increases blood flow by, e.g., about 10% to about 100%, about 20% to about 100%, about 30% to about 100%, about 40% to about 100%, about 50% to about 100%, about 60% to about 100%, about 70% to about 100%, or about 80% to about 100%.

In other aspects of this embodiment, a therapeutically effective amount of a molecular carbon dioxide increases blood flow by, e.g., at least 10%, at least 20%, at least 30%, at least 40%, at least 50%, at least 60%, at least 70%, at least 80%, at least 90% or at least 100% for about 5 minutes of more, about 15 minutes or more, about 30 minutes or more, about 45 minutes or more, about 60 minutes or more, about 75 minutes or more, about 90 minutes or more, about 105 minutes or more, about 120 minutes or more, about 135 minutes or more, about 150 minutes or more, about 165 minutes or more, about 180 minutes or more, about 195 minutes or more, about 210 minutes or more, about 225 minutes or more, or about 240 minutes or more. In yet other aspects of this embodiment, a therapeutically effective amount of a molecular carbon dioxide increases blood flow by, e.g., about 10% to about 100%, about 20% to about 100%, about 30% to about 100%, about 40% to about 100%, about 50% to about 100%, about 60% to about 100%, about 70% to about 100%, or about 80% to about 100% for about 5 minutes of more, about 15 minutes or more, about 30 minutes or more, about 45 minutes or more, about 60 minutes or more, about 75 minutes or more, about 90 minutes or more, about 105 minutes or more, about 120 minutes or more, about 135 minutes or more, about 150 minutes or more, about 165 minutes or more, about 180 minutes or more, about 195 minutes or more, about 210 minutes or more, about 225 minutes or more, or about 240 minutes or more.

In other aspects of this embodiment, a therapeutically effective amount of a molecular carbon dioxide increases blood flow by, e.g., at least 10%, at least 20%, at least 30%, at least 40%, at least 50%, at least 60%, at least 70%, at least 80%, at least 90% or at least 100% for about 5 minutes to about 30 minutes, about 5 minutes to about 60 minutes, about 5 minutes to about 90 minutes, about 5 minutes to about 120 minutes, about 5 minutes to about 150 minutes, about 5 minutes to about 180 minutes, about 5 minutes to about 210 minutes, about 5 minutes to about 240 minutes, about 15 minutes to about 30 minutes, about 15 minutes to about 60 minutes, about 15 minutes to about 90 minutes, about 15 minutes to about 120 minutes, about 15 minutes to about 150 minutes, about 15 minutes to about 180 minutes, about 15 minutes to about 210 minutes, about 15 minutes to about 240 minutes, about 30 minutes to about 60 minutes, about 30 minutes to about 90 minutes, about 30 minutes to about 120 minutes, about 30 minutes to about 150 minutes, about 30 minutes to about 180 minutes, about 30 minutes to about 210 minutes, or about 30 minutes to about 240 minutes. In yet other aspects of this embodiment, a therapeutically effective amount of a molecular carbon dioxide increases blood flow by, e.g., about 10% to about 100%, about 20% to about 100%, about 30% to about 100%, about 40% to about 100%, about 50% to about 100%, about 60% to about 100%, about 70% to about 100%, or about 80% to about 100% for about 5 minutes to about 30 minutes, about 5 minutes to about 60 minutes, about 5 minutes to about 90 minutes, about 5 minutes to about 120 minutes, about 5 minutes to about 150 minutes, about 5 minutes to about 180 minutes, about 5 minutes to about 210 minutes, about 5 minutes to about 240 minutes, about 15 minutes to about 30 minutes, about 15 minutes to about 60 minutes, about 15 minutes to about 90 minutes, about 15 minutes to about 120 minutes, about 15 minutes to about 150 minutes, about 15 minutes to about 180 minutes, about 15 minutes to about 210 minutes, about 15 minutes to about 240 minutes, about 30 minutes to about 60 minutes, about 30 minutes to about 90 minutes, about 30 minutes to about 120 minutes, about 30 minutes to about 150 minutes, about 30 minutes to about 180 minutes, about 30 minutes to about 210 minutes, or about 30 minutes to about 240 minutes.

In another embodiment, a therapeutically effective amount of a molecular carbon dioxide decreases blood pressure. In aspects of this embodiment, a therapeutically effective amount of a molecular carbon dioxide decreases blood pressure by, e.g., at least 10%, at least 20%, at least 30%, at least 40%, at least 50%, at least 60%, at least 70%, at least 80%, at least 90% or at least 100%. In other aspects of this embodiment, a therapeutically effective amount of a molecular carbon dioxide decreases blood pressure by, e.g., about 10% to about 100%, about 20% to about 100%, about 30% to about 100%, about 40% to about 100%, about 50% to about 100%, about 60% to about 100%, about 70% to about 100%, or about 80% to about 100%.

In other aspects of this embodiment, a therapeutically effective amount of a molecular carbon dioxide decreases blood pressure by, e.g., at least 10%, at least 20%, at least 30%, at least 40%, at least 50%, at least 60%, at least 70%, at least 80%, at least 90% or at least 100% for about 5 minutes of more, about 15 minutes or more, about 30 minutes or more, about 45 minutes or more, about 60 minutes or more, about 75 minutes or more, about 90 minutes or more, about 105 minutes or more, about 120 minutes or more, about 135 minutes or more, about 150 minutes or more, about 165 minutes or more, about 180 minutes or more, about 195 minutes or more, about 210 minutes or more, about 225 minutes or more, or about 240 minutes or more. In yet other aspects of this embodiment, a therapeutically effective amount of a molecular carbon dioxide decreases blood pressure by, e.g., about 10% to about 100%, about 20% to about 100%, about 30% to about 100%, about 40% to about 100%, about 50% to about 100%, about 60% to about 100%, about 70% to about 100%, or about 80% to about 100% for about 5 minutes of more, about 15 minutes or more, about 30 minutes or more, about 45 minutes or more, about 60 minutes or more, about 75 minutes or more, about 90 minutes or more, about 105 minutes or more, about 120 minutes or more, about 135 minutes or more, about 150 minutes or more, about 165 minutes or more, about 180 minutes or more, about 195 minutes or more, about 210 minutes or more, about 225 minutes or more, or about 240 minutes or more.

In other aspects of this embodiment, a therapeutically effective amount of a molecular carbon dioxide decreases blood pressure by, e.g., at least 10%, at least 20%, at least 30%, at least 40%, at least 50%, at least 60%, at least 70%, at least 80%, at least 90% or at least 100% for about 5 minutes to about 30 minutes, about 5 minutes to about 60 minutes, about 5 minutes to about 90 minutes, about 5 minutes to about 120 minutes, about 5 minutes to about 150 minutes, about 5 minutes to about 180 minutes, about 5 minutes to about 210 minutes, about 5 minutes to about 240 minutes, about 15 minutes to about 30 minutes, about 15 minutes to about 60 minutes, about 15 minutes to about 90 minutes, about 15 minutes to about 120 minutes, about 15 minutes to about 150 minutes, about 15 minutes to about 180 minutes, about 15 minutes to about 210 minutes, about 15 minutes to about 240 minutes, about 30 minutes to about 60 minutes, about 30 minutes to about 90 minutes, about 30 minutes to about 120 minutes, about 30 minutes to about 150 minutes, about 30 minutes to about 180 minutes, about 30 minutes to about 210 minutes, or about 30 minutes to about 240 minutes. In yet other aspects of this embodiment, a therapeutically effective amount of a molecular carbon dioxide decreases blood pressure by, e.g., about 10% to about 100%, about 20% to about 100%, about 30% to about 100%, about 40% to about 100%, about 50% to about 100%, about 60% to about 100%, about 70% to about 100%, or about 80% to about 100% for about 5 minutes to about 30 minutes, about 5 minutes to about 60 minutes, about 5 minutes to about 90 minutes, about 5 minutes to about 120 minutes, about 5 minutes to about 150 minutes, about 5 minutes to about 180 minutes, about 5 minutes to about 210 minutes, about 5 minutes to about 240 minutes, about 15 minutes to about 30 minutes, about 15 minutes to about 60 minutes, about 15 minutes to about 90 minutes, about 15 minutes to about 120 minutes, about 15 minutes to about 150 minutes, about 15 minutes to about 180 minutes, about 15 minutes to about 210 minutes, about 15 minutes to about 240 minutes, about 30 minutes to about 60 minutes, about 30 minutes to about 90 minutes, about 30 minutes to about 120 minutes, about 30 minutes to about 150 minutes, about 30 minutes to about 180 minutes, about 30 minutes to about 210 minutes, or about 30 minutes to about 240 minutes.

In other aspects of this embodiment, a therapeutically effective amount of a molecular carbon dioxide decreases blood pressure by, e.g., at least 10%, at least 20%, at least 30%, at least 40%, at least 50%, at least 60%, at least 70%, at least 80%, at least 90% or at least 100% for about 4 hours or more, about 6 hours or more, about 8 hours or more, about 10 hours or more, about 12 hours or more, about 18 hours or more, or about 24 hours or more. In yet other aspects of this embodiment, a therapeutically effective amount of a molecular carbon dioxide decreases blood pressure by, e.g., about 10% to about 100%, about 20% to about 100%, about 30% to about 100%, about 40% to about 100%, about 50% to about 100%, about 60% to about 100%, about 70% to about 100%, or about 80% to about 100% for about 4 hours or more, about 6 hours or more, about 8 hours or more, about 10 hours or more, about 12 hours or more, about 18 hours or more, or about 24 hours or more.

Aspects of the present specification disclose, in part, a condition. A condition includes an imperfection, a defect, a disease, and/or a disorder for which relief is sought by the individual suffering from the condition. In another aspect, a condition includes an imperfection, a defect, a disease, and/or a disorder related to low blood flow and oxygen delivery for which relief is sought by the individual suffering from the condition. A condition includes, without limitation, an ischemia, a hypertension, a cardiovascular disorder, treating a diabetic disorder, a wound, a chronic inflammation, an arthritis, a migraine, a cellulite disorder, a pale skin disorder, and a cosmesis disorder. In an aspect, the present specification discloses a use of a substance including a supersaturated amount of dissolved gas to treat a condition. As such, the transdermal delivery device is useful for cosmetic, medical and veterinarian applications. An individual is typically a mammal and this term includes a human being.

An adequate flow of oxygen-rich blood in microcirculation is critical to proper body function. For example, better blood flow is important in maintaining cardiovascular health. The dramatic rise in recent years of the incidence of cardiovascular disease, with more than 1 in 3 U.S. adults now suffering from this life-threatening condition, has resulted in an epidemic of problems related to restricted blood flow. The rapidly growing incidence of obesity has exacerbated this problem. In addition to the highest profile issues accompanying poor blood flow, such as heart attack and stroke, poor blood flow is potentially linked to such conditions as edema, kidney damage, brain function, memory loss, sexual function, muscular performance, limb ischemia, non-healing wounds, diabetic ulcers, and stroke. An adequate flow of oxygen-rich blood in microcirculation is also important in detoxifying the body while improving overall skin health from the inside out. Additional effects of increased oxygen include reducing stress, and reducing the appearance of fat, cellulite, wrinkles, and scars.

Although the body requires oxygen for metabolism, low oxygen levels normally may not stimulate breathing. However, carbon dioxide may be one of the mediators of local auto-regulation of blood supply. If carbon dioxide levels are high, the capillaries may expand to allow a greater blood flow to that tissue. Thus, in one aspect of the present specification, the device disclosed herein is an extracorporeal device that functions by transdermally delivering molecular carbon dioxide to the bloodstream through the skin's pores and sweat glands. The supersaturated dissolved molecular carbon dioxide water vapor mixes easily in the watery sweat pores and glands where it reaches microcirculation instantly. Through the Bohr Effect (oxygen curve shift), the carbon dioxide initiates a gas-exchange balancing process at the microvascular level which facilitates oxygen unloading when blood cells exchange carbon dioxide and water and decreases blood pH in areas with lower oxygen perfusion levels, such as, e.g., areas of low blood flow. As red blood cells sense local oxygen demand, the increased molecular oxygen triggers release of vasodilatory agents from these cells to match local blood flow requirements. This release dilates the blood vessels greatly improves circulation and blood flow of oxygen-rich blood into the area. This increased blood flow results in better oxygenated cells and tissues thereby providing nutrient support for many bodily processes and detoxification of waste products. Thus, molecular carbon dioxide is a signal that ultimately directs the body to increase blood flow and oxygen levels in areas where demand is the highest.

The average density of sweat pores varies greatly with the individual and body site. The palmer surfaces, palms and finger, and the plantar surfaces, soles of the feet and the toes have an average of 2,700 pores per square inch of ridge friction skin surface. This compares to approximately 400 pores per square inch of the balance of the body's skin surface. The total number of sweat pores distributed over the entire body has been estimated at from 1.6 to four million. Because human palms, fingers, toes, and soles of the feet have seven times more pores than elsewhere on the body, these regions are ideal for delivering the treatments disclosed herein, while the circulatory system almost instantly distributes oxygen-rich red blood cells in the entire body.

In an embodiment, the route of administration is a transdermal route. In aspect of this embodiment, a therapeutic agent disclosed herein is transdermally delivered to a finger, a toe, a palm of a hand, or a sole of a foot of the individual. In other aspects of this embodiment, a therapeutic agent disclosed herein is transdermally delivered to a skin surface of the individual. In yet other aspects of this embodiment, a therapeutic agent disclosed herein is transdermally delivered to a skin surface of the individual at or in the vicinity of a condition.

In an embodiment, a method of treating an ischemia comprises the step of administering a composition comprising a substance including a therapeutically effective amount of dissolved gas using a transdermal delivery device as disclosed herein to the individual suffering from the ischemia, wherein the administration of the composition reduces a symptom associated with the ischemia. Ischemia is a restriction in blood supply, generally due to factors in the blood vessels, with resultant damage or dysfunction of tissue. Ischemia is a feature of heart diseases, transient ischemic attacks, cerebrovascular accidents, ruptured sensitive to inadequate blood supply. Ischemia in brain tissue, for example due to stroke or head injury, causes a process called the ischemic cascade to be unleashed, in which proteolytic enzymes, reactive oxygen species, and other harmful chemicals damage and may ultimately kill brain tissue. Ischemia is particularly prevalent in patients with diabetes and obesity, whose poor blood flow often results in an insufficient supply of oxygen to tissues in the lower limbs, causing skin ulcers and non-healing wounds that often lead to amputations. Better blood flow can help these wounds heal and save many potentially lost limbs. There are various types of ischemia, organized by the organ experiencing the ischemic insult, including, without limitation, cardiac ischemia, bowel ischemia, brain ischemia, limb ischemia and cutaneous ischemia. Pain is a common symptom associated with ischemia, but does not always occur. Brain ischemia can cause cognitive, sensory or motor problems. Heart attacks and intestinal ischemia can cause nausea and vomiting. Peripheral ischemia can cause pallor, bluish discoloration, or darkening of the skin of the nose, ears, fingers, toes, or other surface areas. A treatment disclosed herein can improve blood circulation and delivery of oxygen-rich blood to the ischemic tissue, thereby treating the ischemia.

In an aspect of this embodiment, a method of treating an ischemia comprises the step of administering a composition comprising a substance including a therapeutically effective amount of a dissolved molecular carbon dioxide using the transdermal delivery disclosed herein to the individual suffering from the ischemia, wherein the administration of the composition reduces a symptom associated with the ischemia.

In another embodiment, a method of treating a hypertension comprises the step of administering a composition comprising a substance including a therapeutically effective amount of dissolved gas using a transdermal delivery device as disclosed herein to the individual suffering from the hypertension, wherein the administration of the composition reduces a symptom associated with the hypertension. Hypertension is a chronic medical condition in which the blood pressure in the arteries is elevated, requiring the heart to work harder than normal to circulate blood through the blood vessels. Normal blood pressure is at or below 120/80 mmHg. High blood pressure is said to be present if it is persistently above 140/90 mmHg. Hypertension, includes, without limitation, hypertension stage I, hypertension stage II, and isolated systolic hypertension. Symptoms of hypertension include, without limitation, headache, dizziness, blurred vision, nausea and vomiting, chest pain, shortness of breath, heart attack, heart failure, stroke or transient ischemic attack (TIA), kidney failure, eye damage with progressive vision loss, peripheral arterial disease causing leg pain with walking (claudication), aneurysms, and any combination thereof. A treatment disclosed herein can improve blood circulation and delivery of oxygen-rich blood to the body, thereby lowering blood pressure and treating the hypertension.

In an aspect of this embodiment, a method of treating a hypertension comprises the step of administering a composition comprising a substance including a therapeutically effective amount of a dissolved molecular carbon dioxide using the transdermal delivery device disclosed herein to the individual suffering from the hypertension, wherein the administration of the composition reduces a symptom associated with the hypertension.

In aspects of this embodiment, administration of the composition reduces blood pressure by, e.g., at least 10%, at least 20%, at least 30%, at least 40%, at least 50%, at least 60%, at least 70%, at least 80%, at least 90% or at least 100%. In other aspects of this embodiment, administration of the composition reduces blood pressure by, e.g., about 10% to about 100%, about 20% to about 100%, about 30% to about 100%, about 40% to about 100%, about 50% to about 100%, about 60% to about 100%, about 70% to about 100%, or about 80% to about 100%.

In other aspects of this embodiment, administration of the composition reduces blood pressure by, e.g., at least 10%, at least 20%, at least 30%, at least 40%, at least 50%, at least 60%, at least 70%, at least 80%, at least 90% or at least 100% for about 5 minutes of more, about 15 minutes or more, about 30 minutes or more, about 45 minutes or more, about 60 minutes or more, about 75 minutes or more, about 90 minutes or more, about 105 minutes or more, about 120 minutes or more, about 135 minutes or more, about 150 minutes or more, about 165 minutes or more, about 180 minutes or more, about 195 minutes or more, about 210 minutes or more, about 225 minutes or more, or about 240 minutes or more. In yet other aspects of this embodiment administration of the composition reduces blood pressure by, e.g., about 10% to about 100%, about 20% to about 100%, about 30% to about 100%, about 40% to about 100%, about 50% to about 100%, about 60% to about 100%, about 70% to about 100%, or about 80% to about 100% for about 5 minutes of more, about 15 minutes or more, about 30 minutes or more, about 45 minutes or more, about 60 minutes or more, about 75 minutes or more, about 90 minutes or more, about 105 minutes or more, about 120 minutes or more, about 135 minutes or more, about 150 minutes or more, about 165 minutes or more, about 180 minutes or more, about 195 minutes or more, about 210 minutes or more, about 225 minutes or more, or about 240 minutes or more.

In other aspects of this embodiment, administration of the composition reduces blood pressure by, e.g., at least 10%, at least 20%, at least 30%, at least 40%, at least 50%, at least 60%, at least 70%, at least 80%, at least 90% or at least 100% for about 5 minutes to about 30 minutes, about 5 minutes to about 60 minutes, about 5 minutes to about 90 minutes, about 5 minutes to about 120 minutes, about 5 minutes to about 150 minutes, about 5 minutes to about 180 minutes, about 5 minutes to about 210 minutes, about 5 minutes to about 240 minutes, about 15 minutes to about 30 minutes, about 15 minutes to about 60 minutes, about 15 minutes to about 90 minutes, about 15 minutes to about 120 minutes, about 15 minutes to about 150 minutes, about 15 minutes to about 180 minutes, about 15 minutes to about 210 minutes, about 15 minutes to about 240 minutes, about 30 minutes to about 60 minutes, about 30 minutes to about 90 minutes, about 30 minutes to about 120 minutes, about 30 minutes to about 150 minutes, about 30 minutes to about 180 minutes, about 30 minutes to about 210 minutes, or about 30 minutes to about 240 minutes. In yet other aspects of this embodiment, administration of the composition reduces blood pressure by, e.g., about 10% to about 100%, about 20% to about 100%, about 30% to about 100%, about 40% to about 100%, about 50% to about 100%, about 60% to about 100%, about 70% to about 100%, or about 80% to about 100% for about 5 minutes to about 30 minutes, about 5 minutes to about 60 minutes, about 5 minutes to about 90 minutes, about 5 minutes to about 120 minutes, about 5 minutes to about 150 minutes, about 5 minutes to about 180 minutes, about 5 minutes to about 210 minutes, about 5 minutes to about 240 minutes, about 15 minutes to about 30 minutes, about 15 minutes to about 60 minutes, about 15 minutes to about 90 minutes, about 15 minutes to about 120 minutes, about 15 minutes to about 150 minutes, about 15 minutes to about 180 minutes, about 15 minutes to about 210 minutes, about 15 minutes to about 240 minutes, about 30 minutes to about 60 minutes, about 30 minutes to about 90 minutes, about 30 minutes to about 120 minutes, about 30 minutes to about 150 minutes, about 30 minutes to about 180 minutes, about 30 minutes to about 210 minutes, or about 30 minutes to about 240 minutes.

In other aspects of this embodiment, administration of the composition reduces blood pressure by, e.g., at least 10%, at least 20%, at least 30%, at least 40%, at least 50%, at least 60%, at least 70%, at least 80%, at least 90% or at least 100% for about 4 hours or more, about 6 hours or more, about 8 hours or more, about 10 hours or more, about 12 hours or more, about 18 hours or more, or about 24 hours or more. In yet other aspects of this embodiment, administration of the composition reduces blood pressure by, e.g., about 10% to about 100%, about 20% to about 100%, about 30% to about 100%, about 40% to about 100%, about 50% to about 100%, about 60% to about 100%, about 70% to about 100%, or about 80% to about 100% for about 4 hours or more, about 6 hours or more, about 8 hours or more, about 10 hours or more, about 12 hours or more, about 18 hours or more, or about 24 hours or more.

In yet another embodiment, a method of treating a cardiovascular disorder comprises the step of administering a composition comprising a substance including a therapeutically effective amount of dissolved gas using a transdermal delivery device as disclosed herein to the individual suffering from the cardiovascular disorder, wherein the administration of the composition reduces a symptom associated with the cardiovascular disorder. Cardiovascular disease is any of a number of specific diseases that affect the heart itself and/or the blood vessel system, especially the veins and arteries leading to and from the heart. There are more than 60 types of cardiovascular disorders including, without limitation, a diabetic cardiac conditions, blood vessel inflammation like arteritis, phlebitis, vasculitis; arterial occlusive disease like arteriosclerosis and stenosis, a peripheral arterial disease; an aneurysm; an embolism; a dissection; a pseudoaneurysm; a vascular malformation; a vascular nevus; a thrombosis; a thrombphlebitis; a varicose veins; a stroke. Symptoms of a cardiovascular disorder affecting the heart include, without limitation, chest pain or chest discomfort (angina), pain in one or both arms, the left shoulder, neck, jaw, or back, shortness of breath, dizziness, faster heartbeats, nausea, abnormal heartbeats, feeling very tired. Symptoms of a cardiovascular disorder affecting the brain include, without limitation, sudden numbness or weakness of the face, arm, or leg, especially on one side of the body, sudden confusion or trouble speaking or understanding speech, sudden trouble seeing in one or both eyes, sudden dizziness, difficulty walking, or loss of balance or coordination, sudden severe headache with no known cause. Symptoms of a cardiovascular disorder affecting the legs, pelvis and/or arm include, without limitation, claudication, which is a pain, ache, or cramp in the muscles, and cold or numb feeling in the feet or toes, especially at night. A treatment disclosed herein can improve blood circulation and delivery of oxygen-rich blood to the body, thereby treating the cardiovascular disorder.

In an aspect of this embodiment, a method of treating a cardiovascular disorder comprises the step of administering a composition comprising a substance including a therapeutically effective amount of a dissolved molecular carbon dioxide using the transdermal delivery device disclosed herein to the individual suffering from the cardiovascular disorder, wherein the administration of the composition reduces a symptom associated with the cardiovascular disorder.

In still another embodiment, a method of treating a diabetic disorder comprises the step of administering a composition comprising a substance including a therapeutically effective amount of dissolved gas using a transdermal delivery device as disclosed herein to the individual suffering from the diabetic disorder, wherein the administration of the composition reduces a symptom associated with the diabetic disorder. A diabetes disorder is a group of metabolic diseases in which a person has high blood sugar, either because the body does not produce enough insulin, or because cells do not respond to the insulin that is produced. A diabetic disorder includes, without limitation, a type 1 diabetes, a type 2 diabetes, and a gestational diabetes. Symptoms of a diabetic disorder include, without limitation, increased hunger, unexplained weight loss, frequent urination, high blood sugar, coma, slow wound healing, and persistent wound. A treatment disclosed herein can improve blood circulation and delivery of oxygen-rich blood to the body, thereby treating the diabetic disorder.

In an aspect of this embodiment, a method of treating a diabetic disorder comprises the step of administering a composition comprising a substance including a therapeutically effective amount of a dissolved molecular carbon dioxide using the transdermal delivery device disclosed herein to the individual suffering from the diabetic disorder, wherein the administration of the composition reduces a symptom associated with the diabetic disorder.

In another embodiment, a method of treating a wound comprises the step of administering a composition comprising a substance including a therapeutically effective amount of dissolved gas using a transdermal delivery device as disclosed herein to the individual suffering from the wound, wherein the administration of the composition reduces a symptom associated with the wound. The delivery of oxygen, nutrients, and other substances is necessary to establish essential physiological functions to the area and promote wound healing. A treatment disclosed herein can improve blood circulation and delivery of oxygen-rich blood to the area of the wound in order to facilitate healing, thereby treating the wound.

In an aspect of this embodiment, a method of treating a wound comprises the step of administering a composition comprising a substance including a therapeutically effective amount of a dissolved molecular carbon dioxide using the transdermal delivery device disclosed herein to the individual suffering from the wound, wherein the administration of the composition reduces a symptom associated with the wound.

In another embodiment, a method of treating a chronic inflammation comprises the step of administering a composition comprising a substance including a therapeutically effective amount of dissolved gas using a transdermal delivery device as disclosed herein to the individual suffering from the chronic inflammation, wherein the administration of the composition reduces a symptom associated with the chronic inflammation. Normally, inflammation serves as a protective mechanism by an organism to remove noxious stimuli as well as initiate the healing process for injured tissue. This acute neurogenic inflammation forms the first line of defense by maintaining tissue integrity and contributing to tissue repair. In fact, in the absence of acute neurogenic inflammation, wounds and infections would never heal and progressive destruction of the tissue would compromise the survival of the organism. However, severe or prolonged noxious stimulation results in a chronic inflammatory response provoking injury rather than mediating repair. This inflammation has been implicated in the pathophysiology of a wide range of unrelated disorders which underlie a wide variety of human diseases. Non-limiting examples of disorders exhibiting inflammation as a symptom include, without limitation, an acne, an acid reflux/heartburn, an Alzheimer's disease, an appendicitis, an arteritis, an arthritis, an asthma. an allergy, an allergic rhinitis, an atherosclerosis, an autoimmune disorder, a balanitis, a blepharitis, a bronchiolitis, a bronchitis, a bullous pemphigoid, a ursitis, a cancer, a carditis, a celiac disease, a cellulitis, a cervicitis, a cholangitis, a cholecystitis, a chorioamnionitis, a chronic obstructive pulmonary disease (COPD), a cirrhosis, colitis, a conjunctivitis, cystitis, a common cold, a dacryoadenitis, a dementia, a dermatitis, a dermatomyositis, an eczema, an emphysema, an encephalitis, an endocarditis, an endometritis, an enteritis, an enterocolitis, an epicondylitis, an epididymitis, a fasciitis, a fibrositis, a gastritis, a gastroenteritis, a gingivitis, a glomerulonephritis, a glossitis, a heart disease, a hepatitis, a hidradenitis suppurativa, a high blood pressure, an ileitis, an inflammatory dermatologic disease, an inflammatory neuropathy, an insulin resistance, an interstitial cystitis, an iritis, an ischemic heart disease, a keratitis, a keratoconjunctivitis, a laryngitis, a mastitis, a mastoiditis, a meningitis, a metabolic syndrome (syndrome X), a migraine, a myelitis, a myocarditis, a myositis, a nephritis, an obesity, an omphalitis, an oophoritis, an orchitis, an osteochondritis, an osteopenia, an osteoporosis, an osteitis, an otitis, a pancreatitis, a Parkinson's disease, a parotitis, a pelvic inflammatory disease, a pemphigus vularis, a pericarditis, a peritonitis, a pharyngitis, a phlebitis, a pleuritis, a pneumonitis, a proctitis, a prostatitis, a psoriasis, a pulpitis, a pyelonephritis, a pylephlebitis, a rheumatic fever, a rhinitis, a salpingitis, a sialadenitis, a sinusitis, a spastic colon, a stomatitis, a synovitis, a tendonitis, a tendinosis, a tenosynovitis, a thrombophlebitis, a tonsillitis, a trigonitis, a tumor, an urethritis, an uveitis, a vaginitis, a vasculitis, and a vulvitis. General symptoms of chronic inflammation include, without limitation, fatigue, pain, asthma, swelling of tissue, whereas other symptoms are specific for the particular type of chronic inflammation and are known to a person of ordinary skill. A treatment disclosed herein can improve blood circulation and delivery of oxygen-rich blood to the inflamed area, thereby treating the chronic inflammation.

In an aspect of this embodiment, a method of treating a chronic inflammation comprises the step of administering a composition comprising a substance including a therapeutically effective amount of a dissolved molecular carbon dioxide using the transdermal delivery device disclosed herein to the individual suffering from the chronic inflammation, wherein the administration of the composition reduces a symptom associated with the chronic inflammation.

In yet another embodiment, a method of treating an arthritis comprises the step of administering a composition comprising a substance including a therapeutically effective amount of dissolved gas using a transdermal delivery device as disclosed herein to the individual suffering from the arthritis, wherein the administration of the composition reduces a symptom associated with the arthritis. Arthritis includes a group of more than 100 conditions involving damage to the joints of the body due to the inflammation of the synovium including, without limitation osteoarthritis, rheumatoid arthritis, juvenile idiopathic arthritis, spondyloarthropathies like ankylosing spondylitis, reactive arthritis (Reiter's syndrome), psoriatic arthritis, enteropathic arthritis associated with inflammatory bowel disease, Whipple's disease and Behcet's disease, septic arthritis, gout (also known as gouty arthritis, crystal synovitis, metabolic arthritis), pseudogout (calcium pyrophosphate deposition disease), and Still's disease. Arthritis can affect a single joint (monoarthritis), two to four joints (oligoarthritis) or five or more joints (polyarthritis) and can be either an auto-immune disease or a non-autoimmune disease. Symptoms of arthritis include, without limitation, joint pain, joint swelling, joint stiffness, chills, fever, joint tenderness, joint redness, and loss of appetite. A treatment disclosed herein can improve blood circulation and delivery of oxygen-rich blood to the arthritic area, thereby treating the arthritis.

In an aspect of this embodiment, a method of treating an arthritis comprises the step of administering a composition comprising a substance including a therapeutically effective amount of a dissolved molecular carbon dioxide using the transdermal delivery device disclosed herein to the individual suffering from the arthritis, wherein the administration of the composition reduces a symptom associated with the arthritis.

In still another embodiment, a method of treating a migraine comprises the step of administering a composition comprising a substance including a therapeutically effective amount of dissolved gas using a transdermal delivery device as disclosed herein to the individual suffering from the migraine, wherein the administration of the composition reduces a symptom associated with the migraine. A migraine is a chronic neurological disorder characterized by moderate to severe headaches, and nausea. A migraine includes, without exception, a migraine without aura, a migraine with aura, a menstrual migraine, a migraine equivalent, a complicated migraine, a retinal migraine, an abdominal migraine, or a mixed tension migraine. Symptoms of a migraine include, without limitation, throbbing pain on one side of head, nausea, vomiting, diarrhea, facial pallor, cold hands, cold feet, sensitivity to light, and sensitivity to sound. A treatment disclosed herein can improve blood circulation and delivery of oxygen-rich blood to the brain area, thereby treating the migraine.

In an aspect of this embodiment, a method of treating a migraine comprises the step of administering a composition comprising a substance including a therapeutically effective amount of a dissolved molecular carbon dioxide using the transdermal delivery device disclosed herein to the individual suffering from the migraine, wherein the administration of the composition reduces a symptom associated with the migraine.

In another embodiment, a method of treating a cellulite disorder comprises the step of administering a composition comprising a substance including a therapeutically effective amount of dissolved gas using a transdermal delivery device as disclosed herein to the individual suffering from the cellulite disorder, wherein the administration of the composition reduces a symptom associated with the cellulite disorder. Cellulite is a superficial fat that is located just underneath the top layer of skin. Cellulite occurs when fat cells become too large for the natural fiber compartments which hold the skin, causing these compartments bulge and form uneven layers of fat underneath. A treatment disclosed herein can improve blood circulation and delivery of oxygen-rich blood to the cellulite areas, thereby destroying the fat cells and treating the cellulite disorder.

In an aspect of this embodiment, a method of treating a cellulite disorder comprises the step of administering a composition comprising a substance including a therapeutically effective amount of a dissolved molecular carbon dioxide using the transdermal delivery device disclosed herein to the individual suffering from the cellulite disorder, wherein the administration of the composition reduces a symptom associated with the cellulite disorder.

In yet another embodiment, a method of treating a pale skin disorder comprises the step of administering a composition comprising a substance including a therapeutically effective amount of dissolved gas using a transdermal delivery device as disclosed herein to the individual suffering from the pale skin disorder, wherein the administration of the composition reduces a symptom associated with the pale skin disorder. Pale skin occurs when there is a reduced amount of oxyhemoglobin in skin or mucous membrane. It can develop suddenly or gradually, depending on the cause. A pale color can be caused by illness, emotional shock or stress, stimulant use, lack of exposure to sunlight, anaemia or genetics. A pale skin is more evident on the face and palms. A treatment disclosed herein can improve blood circulation and delivery of oxygen-rich blood to the skin, thereby treating the pale skin.

In an aspect of this embodiment, a method of treating a pale skin disorder comprises the step of administering a composition comprising a substance including a therapeutically effective amount of a dissolved molecular carbon dioxide using the transdermal delivery device disclosed herein to the individual suffering from the pale skin disorder, wherein the administration of the composition reduces a symptom associated with the pale skin disorder.

In yet another embodiment, a method of treating a cosmesis disorder comprises the step of administering a composition comprising a substance including a therapeutically effective amount of dissolved gas using a transdermal delivery device as disclosed herein to the individual suffering from the cosmesis disorder, wherein the administration of the composition reduces a symptom associated with the cosmesis disorder. Cosmesis is the preservation, restoration, or bestowing of bodily beauty. As used herein, the term "cosmesis disorder" refers to a skin condition having an unwanted or undesirable feature that deters from bodily beauty. The skin is the body's largest organ and first line of defense against diseases, chemicals, sunlight, and other environmental agents. Increasing oxygenation and blood flow in the entire skin surface produces a stronger, more resilient barrier to fight off these environmental invaders. Cosmesis disorders include, without limitation, a disease, a defect, or an imperfection of the skin. The location may include any part of the body where skin is present, including, without limitation a face, a neck, an upper arm, a lower arm, a hand, a shoulder, a back, a torso including abdomen, a buttock, an upper leg, a lower leg including calf, a foot, a genital area, or any other body part, region or area. Non-limiting examples of a cosmesis disorder include a skin fold, a skin line, a skin wrinkle, a skin mark, or other size, shape or contour imperfection or defect of the skin. A facial fold, line and/or wrinkle include, without limitation, a glabellar line, a nasolabial line, a perioral line, and/or a marionette line. A treatment disclosed herein can improve blood circulation and delivery of oxygen-rich blood to the area comprising the cosmesis disorder, thereby treating the cosmesis disorder.

In an aspect of this embodiment, a method of treating a cosmesis disorder comprises the step of administering a composition comprising a substance including a therapeutically effective amount of a dissolved molecular carbon dioxide using the transdermal delivery device disclosed herein to the individual suffering from the cosmesis disorder, wherein the administration of the composition reduces a symptom associated with the cosmesis disorder.

In yet another embodiment, a method of treating a fungus comprises the step of administering a composition comprising a substance including a therapeutically effective amount of dissolved gas using a transdermal delivery device as disclosed herein to the individual suffering from the fungus, wherein the administration of the composition reduces a symptom associated with the fungus. In one embodiment, carbon dioxide can be used as a therapeutic gas. A fungus can be located in or on the body. Locations such as nails, toes, fingers, pubic regions and the like can be treated using the delivery device described herein. Fungi can be anaerobic organisms that may only survive in low oxygen environments. Hence, treatment with a therapeutic gas can result in an increased oxygen-rich microcirculatory improvement that can kill and/or treat fungi and the illnesses and symptoms associated with them. In one embodiment, a treatment disclosed herein can improve blood circulation and delivery of oxygen-rich blood to the skin, thereby treating the fungus.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the device, compositions, or methods and uses of treating a condition disclosed herein.

Example 1

Measurement of Blood Flow

A study was conducted to demonstrate that use of the device disclosed herein can improve blood flow in an individual. The treatment was administered by having an individual insert the left thumb into the open-ended delivery outlet of a device disclosed herein creating a seal. The digit will be "bathed" for five minutes with a vapor including supersaturated dissolved molecular carbon dioxide from a canister providing pure, medical-grade carbon dioxide. Nine individuals were examined.

Tissue perfusion in distal arteries was accessed using a SensiLase System (a FDA-cleared device) and measuring Skin Perfusion Pressure (SPP) and Pulse Volume Recording (PVR). SPP is a pressure measurement in mmHg that assess local blood perfusion in capillaries using a laser Doppler to measure reactive hyperemia, which reflects microcirculation for distal arterial blood flow. PVR is a measurement of plethysmography to assess changes in arterial blood volume. A change in capillary blood flow (CBF) is calculated by determining the change in SPP values over time. For this study, the CBF values of all post-treatment measurements were calculated by dividing the post-treatment SPP value by the pre-treatment SPP value. A measurement of SPP was performed on the individual's right toe at six time points 1) 5 minutes before treatment (pre-treatment); 2) 5 minutes post-treatment; 3) 30 minutes post-treatment; 4) 60 minutes post-treatment; 5) 120 minutes post-treatment; and 6) 240 minutes post-treatment.

Results indicate that administration of molecular carbon dioxide increases blood flow in all individuals examined at some point during the time period measured (Table 1). Seven of the nine individuals studied showed an about 25% increase in capillary blood flow over baseline with four of these exhibiting an about 35% or more increase in capillary blood flow (Table 1). In addition, six of the nine patients showed sustained increases in capillary blood flow over the course of the entire 240 minute study.

TABLE 1

Treatment Effects on Blood Flow

| Patient | Pre-Treatment SPP (mmHg) | CBF | Post Treatment (5 min) SPP (mmHg) | CBF | Post Treatment (30 min) SPP (mmHg) | CBF | Post Treatment (60 min) SPP (mmHg) | CBF | Post Treatment (120 min) SPP (mmHg) | CBF | Post Treatment (240 min) SPP (mmHg) | CBF |
|---|---|---|---|---|---|---|---|---|---|---|---|---|
| 1 | 63 | 100% | 71 | 113% | 67 | 106% | 72 | 114% | 67 | 106% | 65 | 103% |
| 2 | 116 | 100% | 132 | 114% | 142 | 114% | 156 | 134% | 138 | 119% | 133 | 115% |
| 3 | 42 | 100% | 52 | 124% | 54 | 124% | 54 | 124% | 58 | 138% | 46 | 110% |
| 4 | 82 | 100% | 85 | 104% | 0 | — | 84 | 102% | 111 | 135% | 98 | 120% |
| 5 | 82 | 100% | 84 | 102% | 92 | 112% | 85 | 104% | 89 | 109% | 111 | 135% |
| 6 | 69 | 100% | 60 | 87% | 75 | 109% | 77 | 112% | 77 | 112% | 32 | 46% |
| 7 | 64 | 100% | 75 | 117% | 58 | 91% | 54 | 84% | 80 | 125% | 61 | 95% |
| 8 | 73 | 100% | 89 | 122% | 87 | 119% | 75 | 103% | 94 | 129% | 76 | 104% |
| 9 | 106 | 100% | 116 | 109% | 97 | 92% | 131 | 124% | 87 | 82% | 91 | 82% |

Example 2

Measurement of Blood Pressure

A study was conducted to demonstrate that use of the device disclosed herein can decrease high blood pressure in an individual. To conduct this study, individuals from the study described in Example 1 had there blood pressure taken. A measurement of both brachial diastolic blood pressure and systolic blood pressure was performed on the individual's right upper arm at six time points 1) 5 minutes before treatment (pre-treatment); 2) 5 minutes post-treatment; 3) 30 minutes post-treatment; 4) 60 minutes post-treatment; 5) 120 minutes post-treatment; and 6) 240 minutes post-treatment.

Results indicated that administration of molecular carbon dioxide decreased blood pressure in all individuals examined at some point during the time period measured (Table 2). Seven of the nine individuals studied showed decreased diastolic and systolic blood pressure over the course of the entire 240 minute study.

TABLE 2

Treatment Effects on Blood Pressure

| | Pre-Treatment | | | | Post Treatment (5 min) | | | | Post Treatment (30 min) | | | |
|---|---|---|---|---|---|---|---|---|---|---|---|---|
| Patient | Brachial Diastolic | Percent | Brachial Systolic | Percent | Brachial Diastolic | Percent | Brachial Systolic | Percent | Brachial Diastolic | Percent | Brachial Systolic | Percent |
| 1 | 76 | 100% | 140 | 100% | 68 | 89% | 112 | 80% | 70 | 92% | 118 | 84% |
| 2 | 72 | 100% | 122 | 100% | 80 | 111% | 112 | 92% | 70 | 87% | 118 | 97% |
| 3 | 80 | 100% | 120 | 100% | 78 | 98% | 110 | 92% | 70 | 88% | 110 | 92% |
| 4 | 68 | 100% | 140 | 100% | 68 | 100% | 132 | 94% | — | — | — | — |
| 5 | 78 | 100% | 110 | 100% | 60 | 77% | 104 | 95% | 58 | 73% | 98 | 89% |
| 6 | 60 | 100% | 104 | 100% | 68 | 113% | 98 | 94% | 62 | 103% | 100 | 96% |
| 7 | 90 | 100% | 140 | 100% | 72 | 80% | 110 | 79% | 78 | 87% | 112 | 80% |
| 8 | 80 | 100% | 126 | 100% | 72 | 80% | 124 | 98% | 80 | 100% | 118 | 94% |
| 9 | 78 | 100% | 138 | 100% | 60 | 77% | 101 | 73% | 52 | 67% | 112 | 81% |

| | Post Treatment (60 min) | | | | Post Treatment (120 min) | | | | Post Treatment (240 min) | | | |
|---|---|---|---|---|---|---|---|---|---|---|---|---|
| Patient | Brachial Diastolic | Percent | Brachial Systolic | Percent | Brachial Diastolic | Percent | Brachial Systolic | Percent | Brachial Diastolic | Percent | Brachial Systolic | Percent |
| 1 | 82 | 108% | 138 | 99% | 68 | 89% | 120 | 86% | 70 | 92% | 118 | 84% |
| 2 | 70 | 97% | 118 | 97% | 70 | 97% | 128 | 105% | 64 | 89% | 108 | 89% |
| 3 | 78 | 98% | 115 | 96% | 60 | 75% | 90 | 75% | 59 | 74% | 113 | 94% |
| 4 | 60 | 88% | 150 | 107% | 49 | 72% | 127 | 91% | 80 | 118% | 140 | 100% |
| 5 | 68 | 87% | 106 | 96% | 62 | 79% | 102 | 93% | 68 | 87% | 112 | 102% |
| 6 | 50 | 83% | 110 | 106% | 70 | 117% | 110 | 106% | 58 | 97% | 108 | 104% |
| 7 | 78 | 87% | 110 | 79% | 65 | 72% | 111 | 79% | 62 | 69% | 112 | 80% |
| 8 | 72 | 90% | 128 | 102 | 69 | 86% | 116 | 92% | 71 | 89% | 118 | 94% |
| 9 | 62 | 79% | 118 | 86% | 68 | 87% | 118 | 86% | 69 | 88% | 117 | 85% |

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A transdermal delivery device comprising:
a) a housing including
  i) an external body shell comprising a fluid chamber assembly access cover movably engaged with the external body shell;
  ii) an interior compartment including an open-ended delivery outlet and a vapor producing assembly compartment; and
  iii) a cartridge retaining container comprising an external covering shell and an internal cartridge compartment configured to hold a compressed gas cartridge, wherein the cartridge retaining container is detachably engaged with the external body shell;
  wherein the vapor producing assembly compartment is located in between the open-ended delivery outlet and the cartridge retaining container; and b) a vapor producing assembly, configured to supersaturate a liquid with gas delivered from the compressed gas cartridge, including
   i) a fluid chamber assembly comprising a fluid container and a removable fluid container cap; and
   ii) a permeation valve configured to reduce the pressure and increase the temperature of a gas removed from the compressed gas cartridge and delivered to the fluid chamber assembly, wherein said pressure is reduced to between 15 psi and 40 psi and said temperature is increased to between 0° C. and 22° C.;
wherein the vapor producing assembly is substantially contained within the vapor producing assembly compartment, the supersaturated amount of dissolved gas in the vapor is about 600 ppm to about 60,000 ppm.

2. The transdermal delivery device of claim 1, wherein the external covering shell defines the internal cartridge compartment.

3. The transdermal delivery device of claim 1, wherein the device further includes a control switch assembly.

4. The transdermal delivery device of claim 3, wherein the control switch assembly is a mechanical switch or an electronic switch.

5. The transdermal delivery device of claim 1, wherein the compressed gas cartridge is a 16 g compressed gas cartridge.

6. The transdermal delivery device of claim 1, wherein the compressed gas cartridge includes a compressed gas.

7. The transdermal delivery device of claim 6, wherein the compressed gas is carbon dioxide.

8. The transdermal delivery device of claim 1, wherein the permeation valve comprises at least one permeable member selected from rubber, cork, textile, porous polymer, densely sintered metal or combinations thereof.

9. The transdermal delivery device of claim 1, wherein the fluid container includes water.

10. A method of administering a therapeutic agent, comprising:
   a) inserting a compressed gas cartridge into the cartridge retaining container of the transdermal delivery device of claim 1;
   b) supersaturating a therapeutic agent with a gas commuted from the gas cartridge in the vapor producing assembly of the transdermal delivery device of claim 1; and
   c) administering the therapeutic agent to a patient.

* * * * *